(12) United States Patent
Davis

(10) Patent No.: US 9,078,512 B2
(45) Date of Patent: Jul. 14, 2015

(54) PORTABLE SELF POWERED LINE MOUNTED CONDUCTOR ICE THICKNESS MEASURING SYSTEM FOR OVERHEAD ELECTRIC POWER LINES

(71) Applicant: Murray W. Davis, Grosse Pointe Woods, MI (US)

(72) Inventor: Murray W. Davis, Grosse Pointe Woods, MI (US)

(*) Notice: Subject to any disclaimer, the term of this patent is extended or adjusted under 35 U.S.C. 154(b) by 0 days.

(21) Appl. No.: 14/108,613

(22) Filed: Dec. 17, 2013

(65) Prior Publication Data

US 2014/0174170 A1   Jun. 26, 2014

Related U.S. Application Data

(60) Provisional application No. 61/740,517, filed on Dec. 21, 2012.

(51) Int. Cl.
| | |
|---|---|
| *A46B 9/02* | (2006.01) |
| *H02G 1/02* | (2006.01) |
| *G01B 11/06* | (2006.01) |
| *G01W 1/14* | (2006.01) |
| *G01R 1/20* | (2006.01) |

(Continued)

(52) U.S. Cl.
CPC ............ *A46B 9/028* (2013.01); *G01B 11/0616* (2013.01); *G01D 11/30* (2013.01); *G01K 13/00* (2013.01); *G01N 27/223* (2013.01); *G01R 1/20* (2013.01); *G01R 1/22* (2013.01); *G01R 19/0084* (2013.01); *G01R 19/0092* (2013.01); *G01R 31/08* (2013.01); *G01W 1/14* (2013.01); *H01F 27/02* (2013.01); *H01F 27/22* (2013.01); *H01F 38/30* (2013.01); *H01R 4/28* (2013.01); *H02G 1/02* (2013.01); *H04N 5/2252* (2013.01); *A46B 2200/3073* (2013.01); *Y10T 29/49117* (2015.01)

(58) Field of Classification Search
CPC ... G01B 11/0616; G01B 11/14; G01C 15/002
USPC ........................ 73/170.16; 356/623; 324/127
See application file for complete search history.

(56) References Cited

U.S. PATENT DOCUMENTS

| | | |
|---|---|---|
| 2,303,824 A | 12/1942 | Comins |
| 2,306,117 A | 12/1942 | Dunlap |

(Continued)

FOREIGN PATENT DOCUMENTS

| | | |
|---|---|---|
| CN | 202041573 | 11/2011 |
| JP | 2003-061752 | 9/2004 |

OTHER PUBLICATIONS

Pradhan, et al., Fault Direction Estimation in Radial Distribution System Using Phase Change in Sequence Current, IEEE Transactions on Power Delivery, vol. 22, No. 4, pp. 2065-2071, Oct. 2007.

(Continued)

*Primary Examiner* — Arleen M Vazquez
*Assistant Examiner* — Brent J Andrews
(74) *Attorney, Agent, or Firm* — Carlson, Gaskey & Olds, P.C.

(57) ABSTRACT

A device for attaching to an electric power line conductor includes an electrically conductive housing having an opening for accepting the power line conductor and is configured to be grounded to the power line conductor. At least one magnetic core is configured to surround the power line conductor and power a power supply module. A laser triangulation distance measuring device is configured to be powered by the power supply module.

25 Claims, 30 Drawing Sheets

(51) Int. Cl.
*G01R 19/00* (2006.01)
*G01R 31/08* (2006.01)
*G01N 27/22* (2006.01)
*H01F 38/30* (2006.01)
*H04N 5/225* (2006.01)
*G01D 11/30* (2006.01)
*G01K 13/00* (2006.01)
*H01F 27/02* (2006.01)
*H01F 27/22* (2006.01)
*H01R 4/28* (2006.01)
*G01R 1/22* (2006.01)

(56) References Cited

U.S. PATENT DOCUMENTS

| | | | |
|---|---|---|---|
| 3,267,507 A | | 8/1966 | Cox |
| 3,622,867 A | | 11/1971 | Topper et al. |
| 3,861,197 A | | 1/1975 | Adler |
| 4,032,842 A | | 6/1977 | Green et al. |
| 4,052,000 A | * | 10/1977 | Honikman ............. 126/592 |
| 4,061,963 A | | 12/1977 | Green |
| 4,234,863 A | | 11/1980 | Shumway et al. |
| 4,242,930 A | | 1/1981 | Myers et al. |
| 4,268,818 A | | 5/1981 | Davis et al. |
| 4,326,316 A | | 4/1982 | Dolenti |
| 4,420,752 A | | 12/1983 | Davis et al. |
| 4,499,417 A | | 2/1985 | Wright et al. |
| 4,546,340 A | | 10/1985 | Kuchuris |
| 4,728,887 A | | 3/1988 | Davis |
| 4,746,241 A | | 5/1988 | Burbank |
| 4,801,937 A | * | 1/1989 | Fernandes ............. 340/870.16 |
| 4,806,855 A | | 2/1989 | Davis |
| 4,827,272 A | | 5/1989 | Davis |
| 5,029,101 A | * | 7/1991 | Fernandes ............. 702/62 |
| 5,140,257 A | * | 8/1992 | Davis ............. 324/106 |
| 5,232,518 A | | 8/1993 | Nath et al. |
| 5,341,088 A | | 8/1994 | Davis |
| 5,351,359 A | | 10/1994 | Golden |
| 5,426,360 A | | 6/1995 | Maraio et al. |
| 5,796,259 A | | 8/1998 | Dickmander |
| 5,883,511 A | | 3/1999 | Foster |
| 6,151,065 A | | 11/2000 | Steed et al. |
| 6,157,160 A | | 12/2000 | Okawa et al. |
| 6,299,824 B1 | | 10/2001 | Mayr et al. |
| 6,713,670 B2 | | 3/2004 | Stern et al. |
| 6,741,069 B1 | | 5/2004 | Klemar et al. |
| 6,924,732 B2 | | 8/2005 | Yahoo |
| 6,983,508 B2 | | 1/2006 | Saurer |
| 7,030,593 B2 | | 4/2006 | Pinkerton et al. |
| 7,127,972 B2 | | 10/2006 | Klein et al. |
| 7,310,109 B2 | | 12/2007 | Dottling et al. |
| 7,412,338 B2 | | 8/2008 | Wynans et al. |
| 7,432,787 B2 | | 10/2008 | Muench et al. |
| 7,545,140 B2 | | 6/2009 | Humphreys et al. |
| 7,557,563 B2 | | 7/2009 | Gunn et al. |
| 7,570,045 B2 | | 8/2009 | Wolfe et al. |
| 7,579,824 B2 | | 8/2009 | Rea |
| 7,706,596 B2 | | 4/2010 | Garvey |
| 8,022,291 B2 | | 9/2011 | Thomsen et al. |
| 8,144,445 B2 | | 3/2012 | Caggiano et al. |
| 8,184,015 B2 | | 5/2012 | Lilien et al. |
| 8,203,328 B2 | | 6/2012 | Bose et al. |
| 8,300,922 B1 | | 10/2012 | Garvey, III |
| 8,320,146 B2 | | 11/2012 | Haines et al. |
| 8,322,332 B2 | | 12/2012 | Rogers |
| 8,400,504 B2 | | 3/2013 | Al-Duwaish et al. |
| RE44,256 E | | 6/2013 | Bright et al. |
| 8,536,857 B2 | | 9/2013 | Nero, Jr. |
| 8,628,211 B2 | | 1/2014 | Jensen et al. |
| 8,686,302 B2 | | 4/2014 | Brasher et al. |
| 2004/0012678 A1 | | 1/2004 | Li |
| 2006/0060007 A1 | * | 3/2006 | Mekhanoshin et al. ..... 73/865.9 |
| 2006/0125469 A1 | * | 6/2006 | Hansen ............. 324/158.1 |
| 2008/0077336 A1 | | 3/2008 | Fernandes |
| 2008/0136403 A1 | | 6/2008 | Deck |
| 2008/0297162 A1 | | 12/2008 | Bright |
| 2009/0009180 A1 | | 1/2009 | Varghai et al. |
| 2009/0207421 A1 | * | 8/2009 | Kelly et al. ............. 356/614 |
| 2009/0212241 A1 | * | 8/2009 | McGeoch ............. 250/504 R |
| 2009/0243876 A1 | | 10/2009 | Lilien et al. |
| 2010/0085036 A1 | | 4/2010 | Banting et al. |
| 2010/0192975 A1 | | 8/2010 | Schweikert |
| 2011/0204879 A1 | | 8/2011 | Peretto |
| 2011/0308566 A1 | | 12/2011 | Johnson |
| 2012/0086804 A1 | | 4/2012 | Ishibashi et al. |
| 2012/0152346 A1 | | 6/2012 | Yang et al. |
| 2013/0022078 A1 | | 1/2013 | Phillips et al. |
| 2013/0179079 A1 | | 7/2013 | Lancaster |
| 2013/0205900 A1 | | 8/2013 | Nulty |
| 2013/0221977 A1 | | 8/2013 | Ukil et al. |
| 2014/0110376 A1 | | 4/2014 | Zahlmann et al. |

OTHER PUBLICATIONS

Eissa, Evaluation of a New Current Directional Protection Technique Using Field Data, IEEE Transactions on Power Delivery, vol. 20, No. 2, pp. 566-572, Apr. 2005.

Ukil, et al., Smart Distribution Protection Using Current-Only Directional Overcurrent Relay, Innovative Smart Grid Technologies Conference Europe, 2010 IEEE PES, pp. 1-7, 2010.

Recloser, available at http://en.wikipedia.org/wiki/Recloser on Feb. 2, 2012.

Digital protective relay, available at http://en.wikipedia.org/wiki/Digital_protective_relay on Jun. 18, 2012.

* cited by examiner

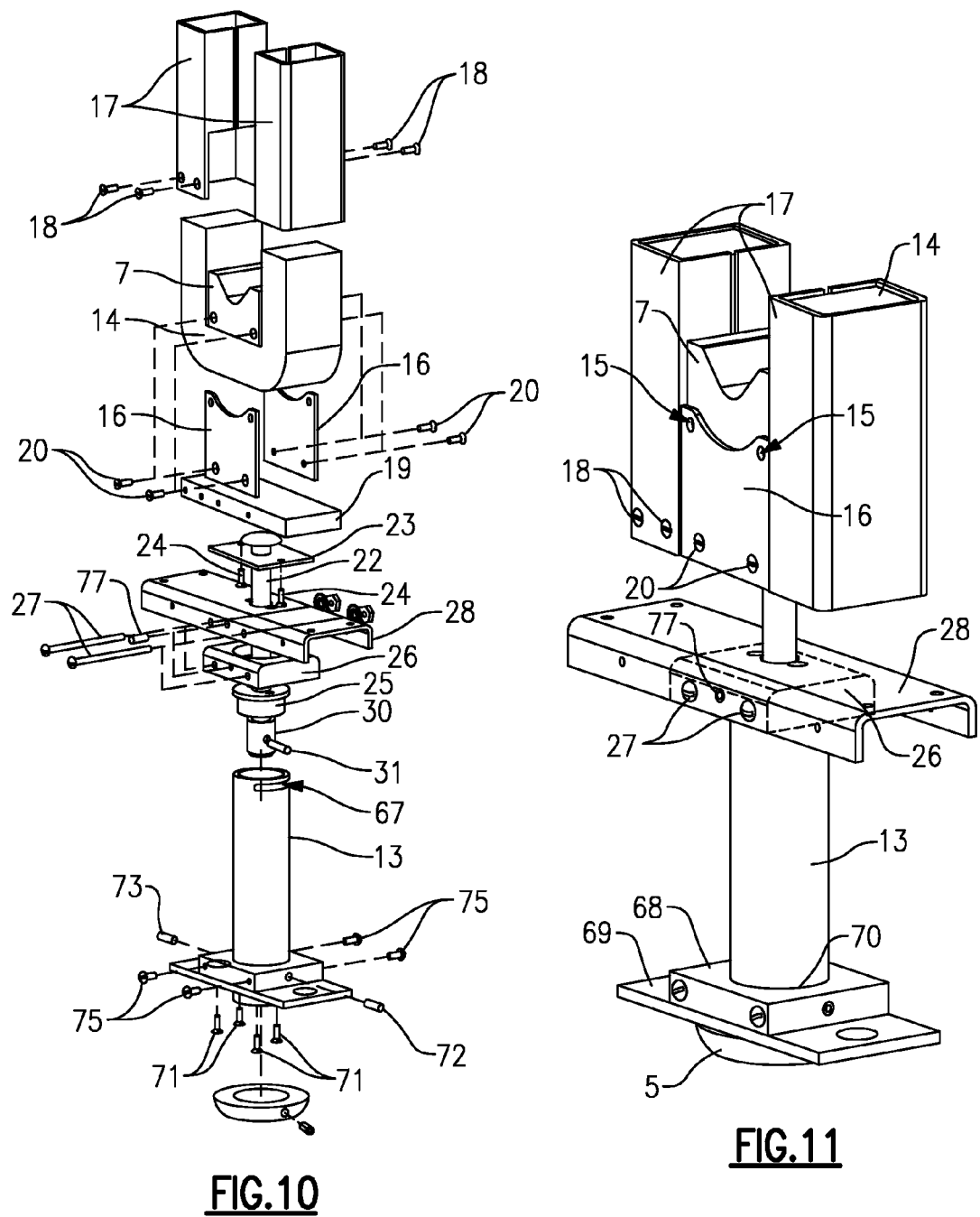

PORTABLE SELF POWERED LINE MOUNTED CONDUCTOR ICE THICKNESS MEASURING SYSTEM FOR OVERHEAD ELECTRIC POWER LINES

CROSS-REFERENCE TO RELATED APPLICATIONS

The application claims priority to U.S. Provisional Application No. 61/740,517 which was filed on Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device which is low maintenance and can be constantly powered independent of weather conditions.

Ice can cause a significant amount of damage to a power system, especially during an ice storm when significant amounts of ice can accumulate on the power lines. The weight of the ice accumulation causes additional tension on overhead power lines resulting in increased line sag and possible line failure. There is a need for a device that can measure and predict ice formation on overhead power lines.

SUMMARY

A device for attaching to an electric power line conductor includes an electrically conductive housing having an opening for accepting the power line conductor and is configured to be grounded to the power line conductor. At least one magnetic core is configured to surround the power line conductor and power a power supply module. A laser triangulation distance measuring device is configured to be powered by the power supply module.

A method of measuring ice thickness on an electric power line conductor includes measuring ice thickness on the electric power line conductor with a laser distance measuring device to determine laser ice thickness measurements. Ice thickness measurements are processed with a sensor electronics module. Data representative of the ice thickness measurements is transmitted to a remote location with an onboard transmitter-receiver unit and an antenna for analysis.

These and other features of the disclosed examples can be understood from the following description and the accompanying drawings, which can be briefly described as follows.

BRIEF DESCRIPTION OF THE DRAWINGS

FIG. 5a illustrates an enlarged view of a keyhole slot.

FIG. 10 illustrates an expanded view of the lower magnetic core, example lead screw assembly, and an example hotstick guide tube.

FIG. 11 illustrates the collapsed view of the lower magnetic core, the lead screw assembly, and the hotstick guide tube.

DETAILED DESCRIPTION

Figure 1:
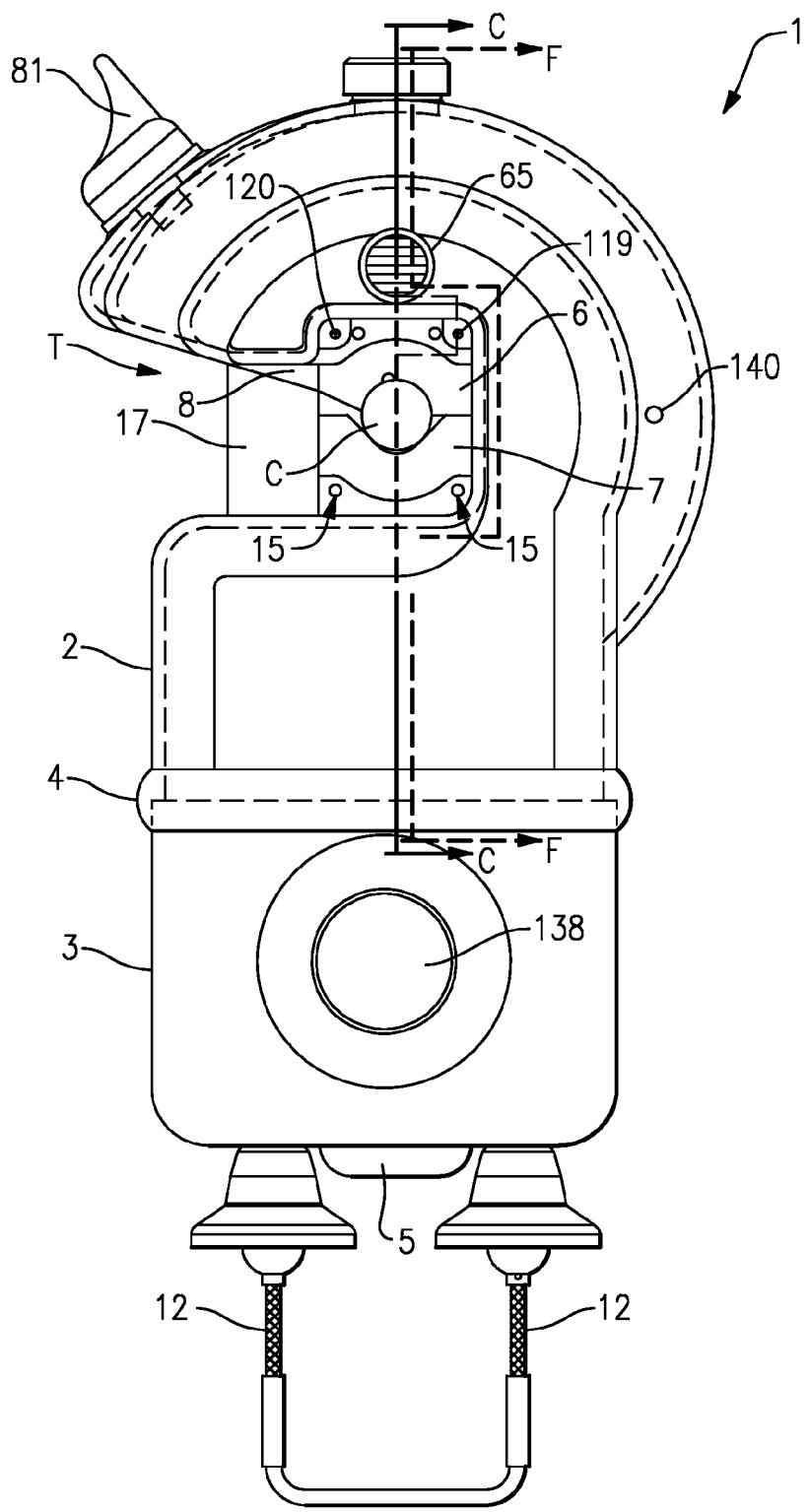
FIG. 1 illustrates a right side view of an example sensor transmitter receiver unit ("STR unit").
Figure 2:
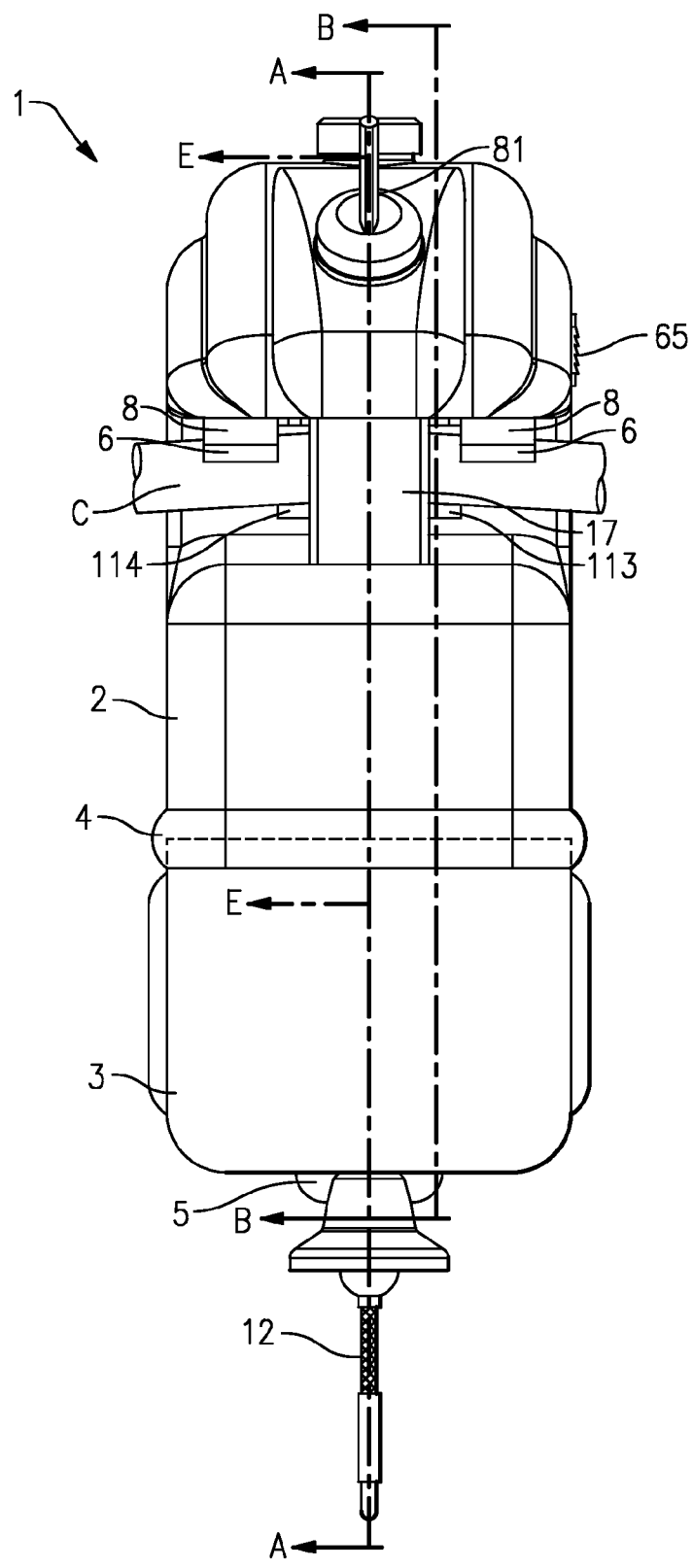
FIG. 2 illustrates a front view of the STR unit of FIG. 1.

FIGS. 1 and 2 illustrate an example sensor transmitter receiver unit ("STR unit") 1 installed on a power line conductor C for measuring and monitoring various parameters of the power line conductor C and its environment. The STR unit 1 is formed from a one piece upper housing 2 and a one piece lower housing 3. The lower housing 3 is accepted into a bead 4 formed on a distal end of the upper housing 2. In this example, the bead 4 which is an integral part of the upper housing 2 is formed by machining a portion of the upper housing 2 to form a groove on the inside of the bead 4. The lower housing 3 is secured to the bead 4 and the upper housing 2 by a collar 5. The collar 5 attaches to a hotstick guide tube 13 (FIG. 3) that is secured to the upper housing 2 and extends through the lower housing 3.

In one example, the upper housing 2 and the lower housing 3 are made of aluminum or other suitable electrically conductive material. The material chosen should accommodate subassembly installation without the use of external surface fasteners which could generate corona discharges due to high voltage being applied to the upper housing 2 and the lower housing 3. The upper housing 2 has the advantage of reducing the number of mating surfaces and eliminating mismatches between multiple cast parts which can generate corona discharges and audible noise due to slightly offset sharp edges of the mating surfaces of the adjacent castings.

Figure 3:
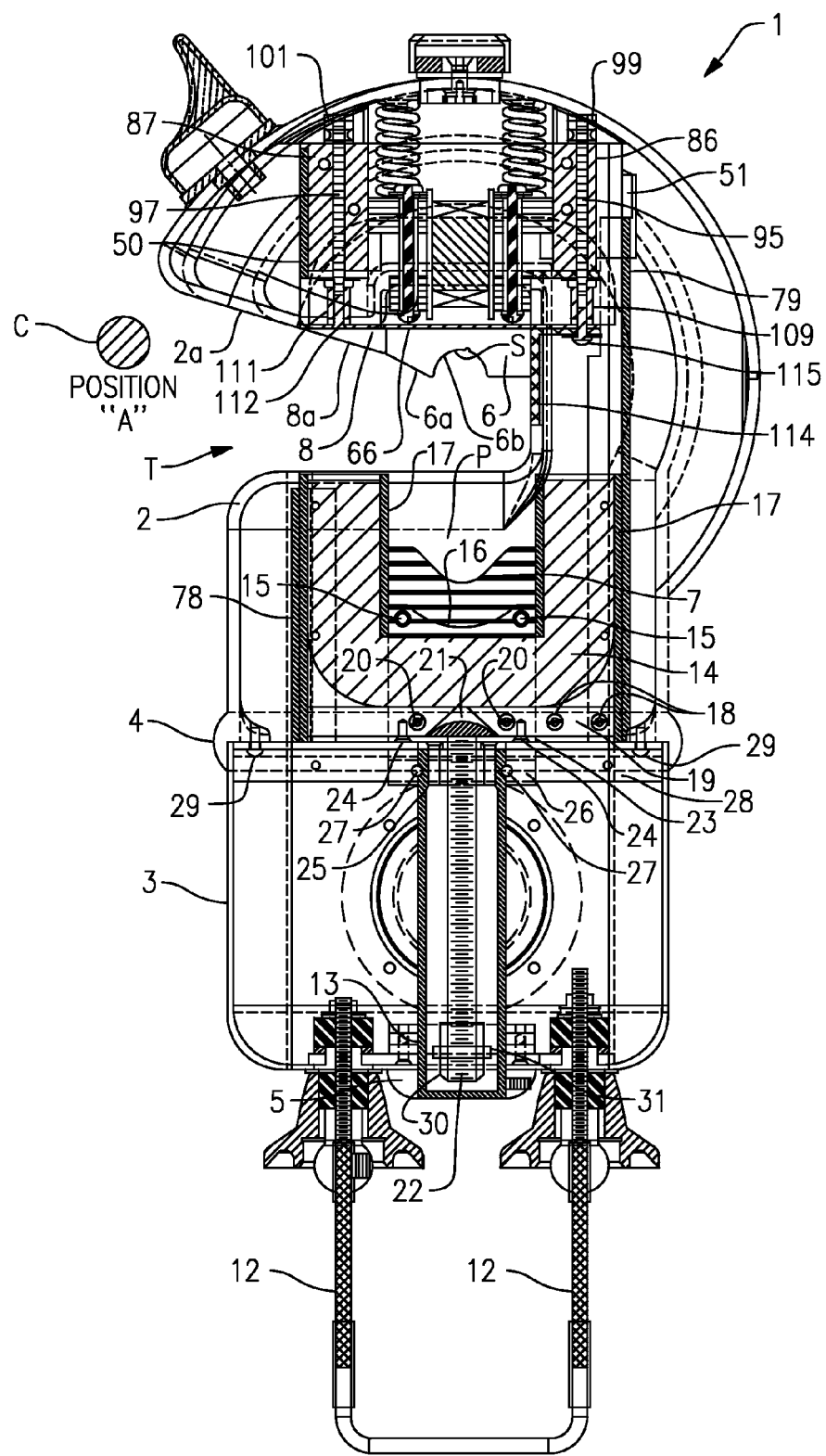
FIG. 3 illustrates a cross-sectional view taken along line A-A of FIG. 2.
Figure 4:
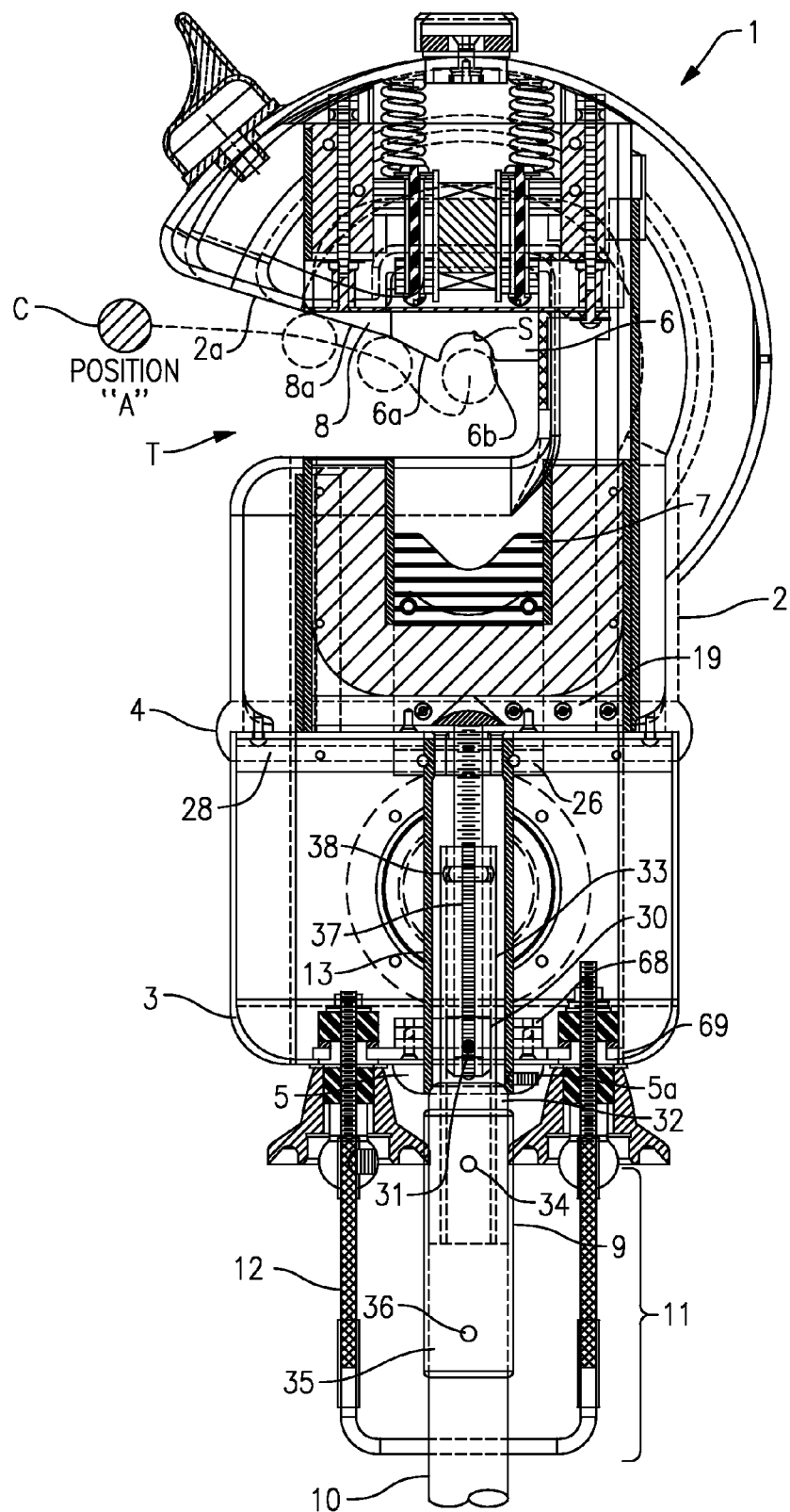
FIG. 4 illustrates a cross-sectional view taken along line A-A of FIG. 2 with an example hotstick.

Referring to FIGS. 3 and 4, before the STR unit 1 is clamped onto the conductor C, a lower jaw 7 is moved to its fully lowered position spaced from upper jaws 6. This allows the conductor C to pass from position "A" of FIG. 3 through a throat T on the left side of the upper housing 2 and onto the upper jaws 6 in position "B" as shown in FIG. 5.

With the lower jaw 7 of the STR unit 1 in its fully lowered position, a specially designed hotstick 10 is inserted into the bottom of the STR unit 1 and inside the hotstick guide tube 13. In this example, the hotstick 10 is made of an electrically insulated material such as fiberglass. The hotstick 10 includes a hotstick driver assembly 9 (FIG. 4) attached to the hotstick 10 with a pin 36. The hotstick 10 provides the required electrical insulation between the hands of the linemen and the energized conductor C. A flexible stirrup assembly 11 (FIG. 4) contains a flexible braided conductor 12 which bends out of the way to allow the hotstick driver assembly 9 to enter a hole in the collar 5. As mentioned earlier, the collar 5 secures the lower housing 3 to the bead 4 on the upper housing 2. The collar 5 is fastened to the hotstick guide tube 13 using the set screw 5a which is screwed into the collar 5 and into a hole in the hotstick guide tube 13.

With the hotstick 10 and the hotstick driver assembly 9 fully engaged inside the hotstick guide tube 13, the STR unit 1 can be lifted by the lineman with the hotstick 10 onto the conductor C while maintaining the STR unit 1 securely attached to the hotstick 10.

Figure 5:
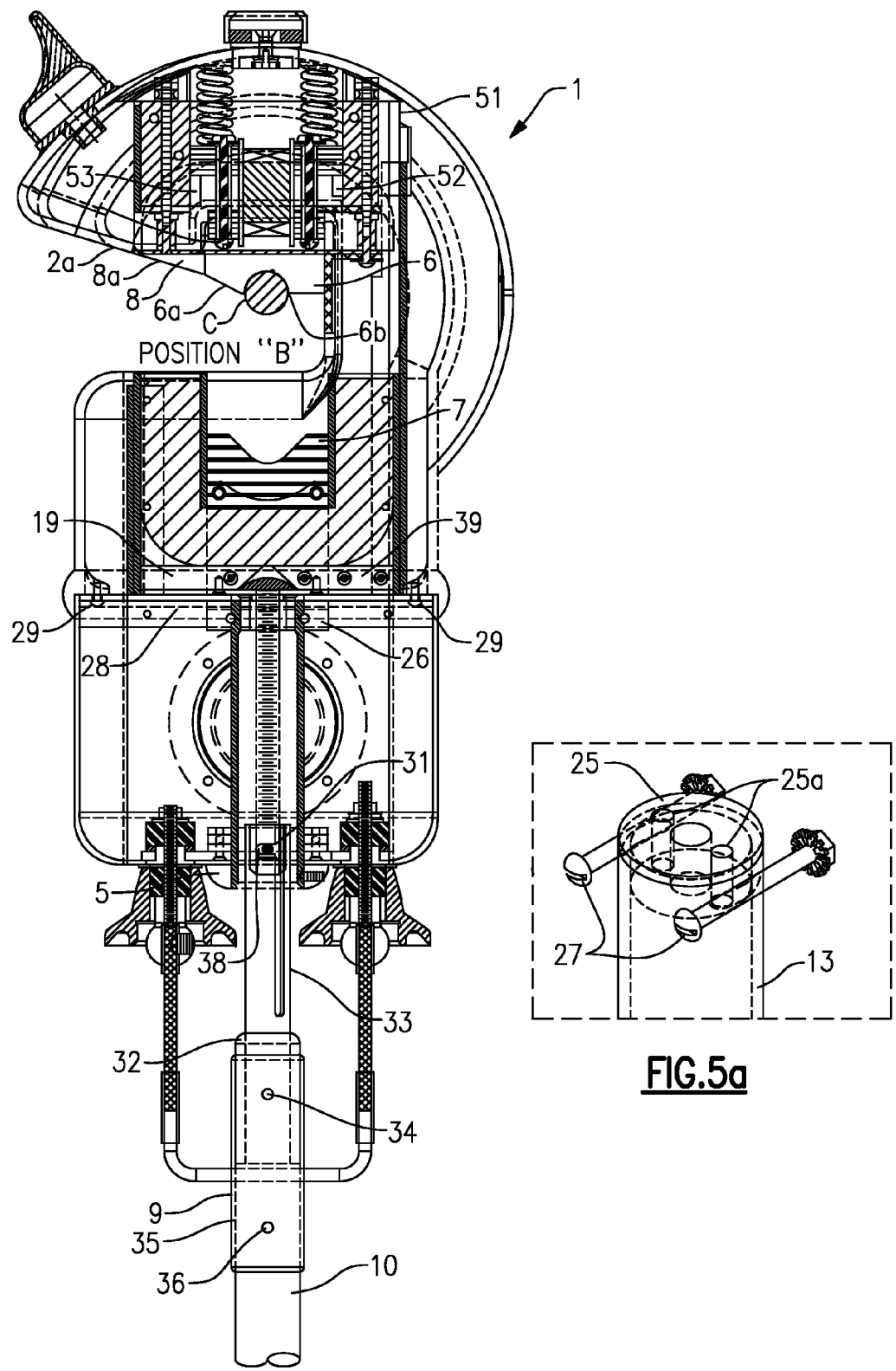
FIG. 5 illustrates another cross-sectional view taken along line A-A of FIG. 2 with the example hotstick.
Figure 14:
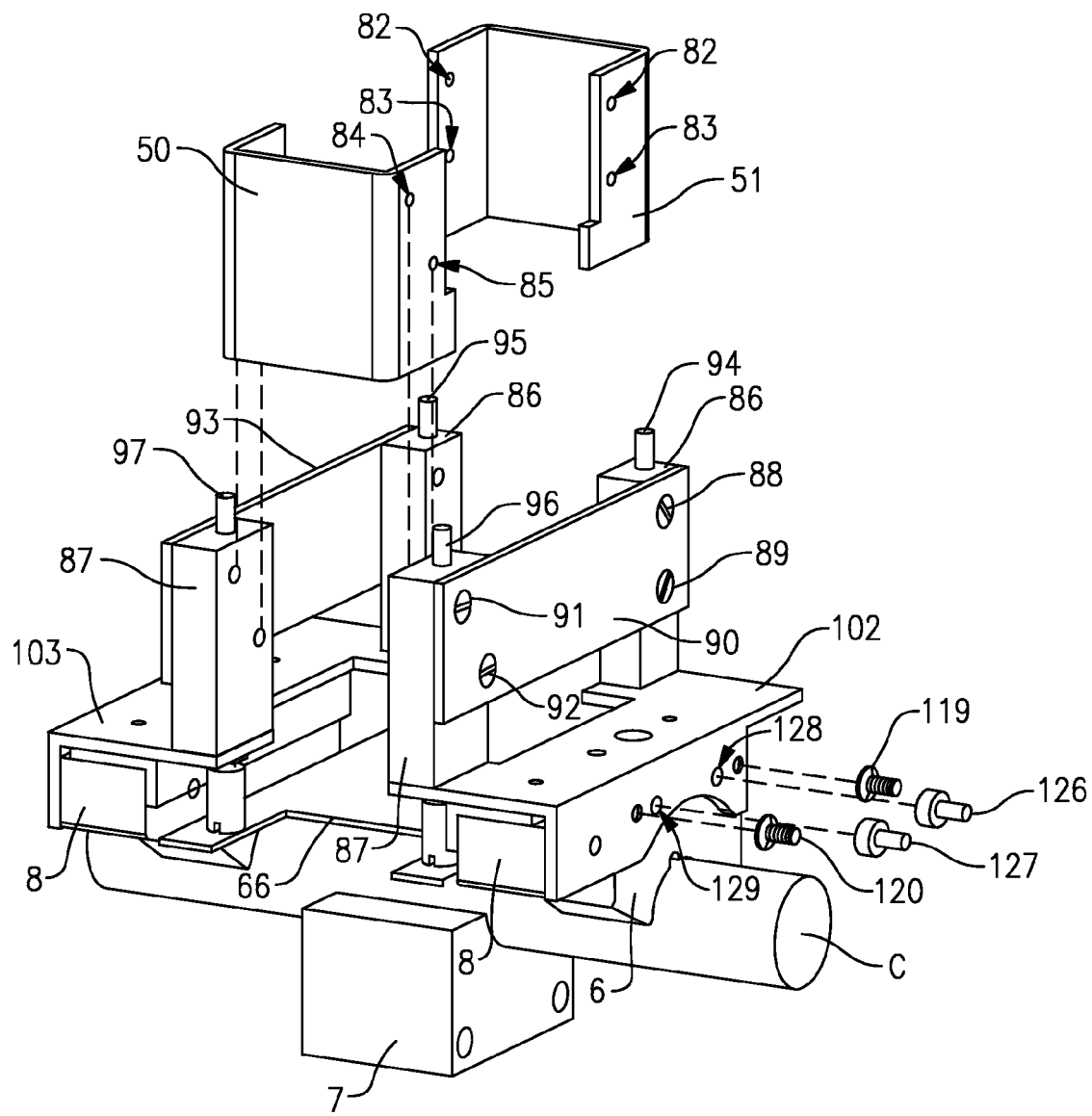
FIG. 14 illustrates an exploded view of example support blocks mounting the upper magnetic core subassembly and example upper and lower jaws.

The upper housing 2 includes two jaw inserts 8, shown in FIGS. 5 and 14, located adjacent the throat T and the upper jaws 6. The two jaw inserts 8 include inclined surfaces 8a and the upper jaws 6 include inclined surfaces 6a. The angle of incline of the inclined surfaces 8a matches the angle of the incline of an inclined surface 2a on the upper housing 2.

The angle of the inclined surfaces 6a is steeper than the angle of the inclined surfaces 8a and the inclined surface 2a to aid in installing the STR Unit 1 on the conductor C. As the conductor C slides across the inclined surfaces 2a and 8a and reaches the steeper incline of the inclined surface 6a, the STR unit 1 will bounce slightly upward and land in a circular notch 6b of the upper jaws 6 (See FIG. 4). This allows a conductor temperature sensor to be mounted vertically and in the middle inside the upper jaws 6 and initially extends slightly below the circular notch 6b for the upper portion of the conductor C. The two different inclined surfaces 6a and 8a of the jaw inserts 8 and upper jaws 6 prevent the conductor temperature sensor S, shown in FIGS. 3 and 4, from becoming damaged since the conductor C firmly lands vertically in the circular notch 6b of the upper jaws 6 and pushes the conductor temperature sensor S up to the inside surface of the circular notch 6b.

In FIG. 3, the lower jaw 7 is located in a pocket P between two legs of a lower magnetic core 14. The lower jaw 7 is held in place with two spring pins 132 and 133 (FIG. 15) located in the lower jaw 7 that snap into two holes 15 in a lower jaw holder 16 (FIGS. 10 and 11) which is attached to a bottom block 19 using two screws 20 (FIG. 3). The bottom block 19 is located adjacent the base of the upper housing 2.

Two identical electrically conductive lower core covers 17 partially surround the two legs of the lower magnetic core 14. The lower core covers 17 are attached to the bottom block 19 on each side of the lower jaw holder 16 using screws 18 of FIG. 3 on the front right side and one set of the screws 18 on the back left side (not shown). The front and back lower jaw holders 16 are both held in place by the four screws 20, two in the front and two in the back. The two legs of the lower magnetic core 14 are totally encased by the two lower core covers 17 and the front and back lower jaw holders 16. Therefore, the lower magnetic core 14 is not exposed to any moisture, such as from rain, snow, and ice that could enter through the throat T of the upper housing 2 (FIG. 3).

The bottom block 19 contains a conical hole 21 in the center which provides a very low friction bearing surface for the semi-circular top of a lead screw 22 (FIG. 3). The lead screw 22 is held in the conical hole 21 with a retainer plate 23 which has a hole in the middle the size of the lead screw 22 diameter and is fastened to the bottom block 19. The lead screw 22 is threaded into the center of a threaded bushing 25. The threaded bushing 25 has a reduced diameter cylindrical lower portion which fits inside the hotstick guide tube 13 and a larger diameter cylindrical top portion of the threaded bushing 25 is supported on the upper end of the hotstick guide tube 13. Both the threaded bushing 25 and the hotstick guide tube 13 are attached to a hotstick guide support 26 using two large through bolts 27 and nuts which are placed through the holes in a bottom support 28.

Referring to FIG. 2, the upper jaws 6 include two spaced apart jaws and the lower jaw 7 includes a single jaw aligned between the two spaced apart upper jaws 6. When lower jaw 7 is clamped onto the conductor C, the conductor C is bent slightly upward as the lower jaw 7 extends upward between the upper jaws 6 creating a bending moment in the conductor C. The bending moment in the conductor C prevents the STR unit 1 from sliding down the conductor C, especially when the STR unit 1 is mounted at the point of attachment adjacent a utility pole or tower where the slope of the conductor C is at its maximum value. Preventing the upper jaws 6 and the lower jaw 7 from sliding down the conductor C at the point of attachment is necessary when the STR unit is being used to measure sag of the power line conductor.

Referring to FIGS. 5 and 5a, the bottom support 28 includes an upside down "U" shaped cross member and is fastened at each end to the upper housing with two large threaded screws 29 on each side. The threaded bushing 25 has two small vertical holes 25a drilled through the threaded bushing 25 on each side of the threaded hole in the middle for the lead screw 22. The vertical holes 25a are countersunk on the top and provide drainage paths for fluid, such as rain water, that can accumulate underneath the bottom block 19 and on top of the bottom support 28 (FIG. 5a). The water then drains through the two vertical holes 25a in the threaded bushing 25 and drops on the inside of the hotstick guide tube 13 and out the bottom of the STR unit 1. Therefore, water will not leak into the lower housing 3.

Figure 6:
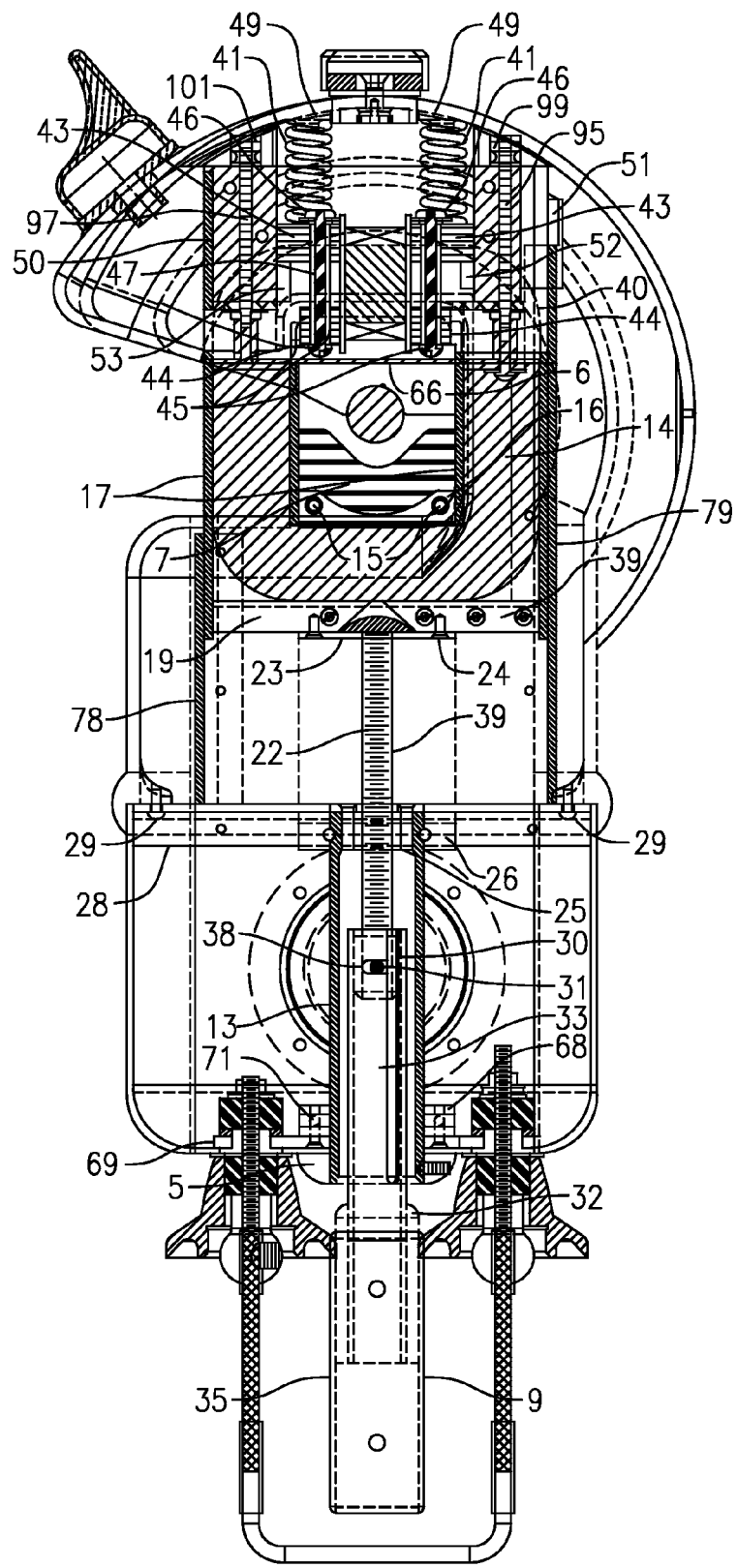
FIG. 6 illustrates another cross-sectional view taken along line A-A of FIG. 2 engaging a conductor.

Referring to FIG. 6, the lead screw 22 has a small diameter hotstick guide 30 which is threaded on the inside and is screwed on the bottom of the lead screw 22. A pin 31 keeps the hotstick guide 30 from turning on the lead screw 22. The hotstick guide 30 prevents the inside of a hotstick lead screw driver 33 from coming into contact with the threads on the lead screw 22 and damaging the internal bore of the lead screw driver 33. It also guides the lead screw driver 33 onto the lead screw 22. When the pin 31 engages the lead screw driver 33 the STR unit 1 is ready for installation on the conductor C.

The hotstick driver assembly 9 includes the lead screw driver 33, a hotstick driver coupling 32, a rivet 34, a hotstick sleeve 35, the pin 36, and the hotstick 10. The hotstick 10 of FIG. 4 rests on the rounded portion of the hotstick driver coupling 32 and the rounded inside bottom of the hotstick guide tube 13. This prevents the lead screw driver 33 from applying pressure to the threaded bushing 25 upon installation of the STR unit 1 on the conductor C. The lead screw driver 33 and the hotstick driver coupling 32 are each fastened to the hotstick sleeve 35 by the rivet 34 and the hotstick sleeve 35 is attached to the hotstick 10 with the pin 36. A long narrow vertical slot in the lead screw driver 33 allows the pin 31 of the lead screw 22 to be engaged with the lead screw driver 33 and is free to slide up or down in the vertical slot 37 as the lead screw is turned to tighten the lower jaw 7 on the conductor C or to loosen the lower jaw 7 from the conductor C to remove the STR unit 1.

When the hotstick driver assembly 9 is engaged with the lead screw 22 as shown in in FIG. 4, the STR unit 1 is raised to position "A" relative to the height of the conductor C. The STR unit 1 is then moved toward the conductor C so that the conductor C passes through the throat T of the upper housing 2 and into position "B" as shown in FIG. 5. Once the STR unit 1 is fully supported by the conductor C in position "B", the hotstick driver assembly 9 is turned clockwise by the installer with the hotstick 10 and allowed to drop down from its position in FIG. 4 to a lower position as in FIG. 5. A horizontal keyhole slot 38 of the lead screw driver 33 is now engaged with the pin 31 of the lead screw 22. With the pin 31 in the horizontal keyhole slot 38, the hotstick driver assembly 9 and the hotstick 10 are secured to the STR unit 1.

In this example, an opening and closing mechanism 39 of FIG. 6 extends the lower jaw 7 upward to secure the STR unit 1 on the conductor C. Additionally, the opening and closing mechanism 39 can also retract the lower jaw 7 to remove the STR unit 1 from the conductor C. The opening and closing mechanism 39 includes the lower magnetic core 14, the lower core covers 17, the lower jaw holders 16, the lower jaw 7, spring pins 132 and 133, the bottom block 19, the retainer plate 23, two fasteners 24, the lead screw 22, the hotstick guide 30, and the pin 31.

FIG. 6 illustrates the keyhole slot 38 on the lead screw driver 33 engaged with the pin 31 on the lead screw 22. As the lead screw 22 is turned clockwise, the opening and closing mechanism 39 moves the lower magnetic core 14 toward an upper magnetic core 40. The upper magnetic core 40 has two large compression springs 41 to bias the upper magnetic core 40 downward. The compression springs 44 provide pressure to hold both the upper magnetic core 40 and the lower magnetic core 14 together to reduce the magnetic reluctance caused by air gaps 54 (FIG. 8) between the upper magnetic core 40 and the lower magnetic core 14.

The hotstick driver assembly 9 can continue to be turned clockwise even after the lower magnetic core 14 begins to mate with the upper magnetic core 40 because the compression springs 41 compress at the top of the upper magnetic core 40. The clockwise motion of the hotstick driver assembly 9 can be achieved either manually or with a battery powered drill or another rotating device, until the lower jaw 7 is tightened onto the conductor C. After the STR unit 1 is mounted on the conductor C, the hotstick 10 is turned slightly to the left, or counterclockwise, and the pin 31 will become disengaged from the horizontal portion of the keyhole slot 38. The hotstick 10 is then free to be removed when the pin 31 aligns with the vertical slot 37.

Figure 7:
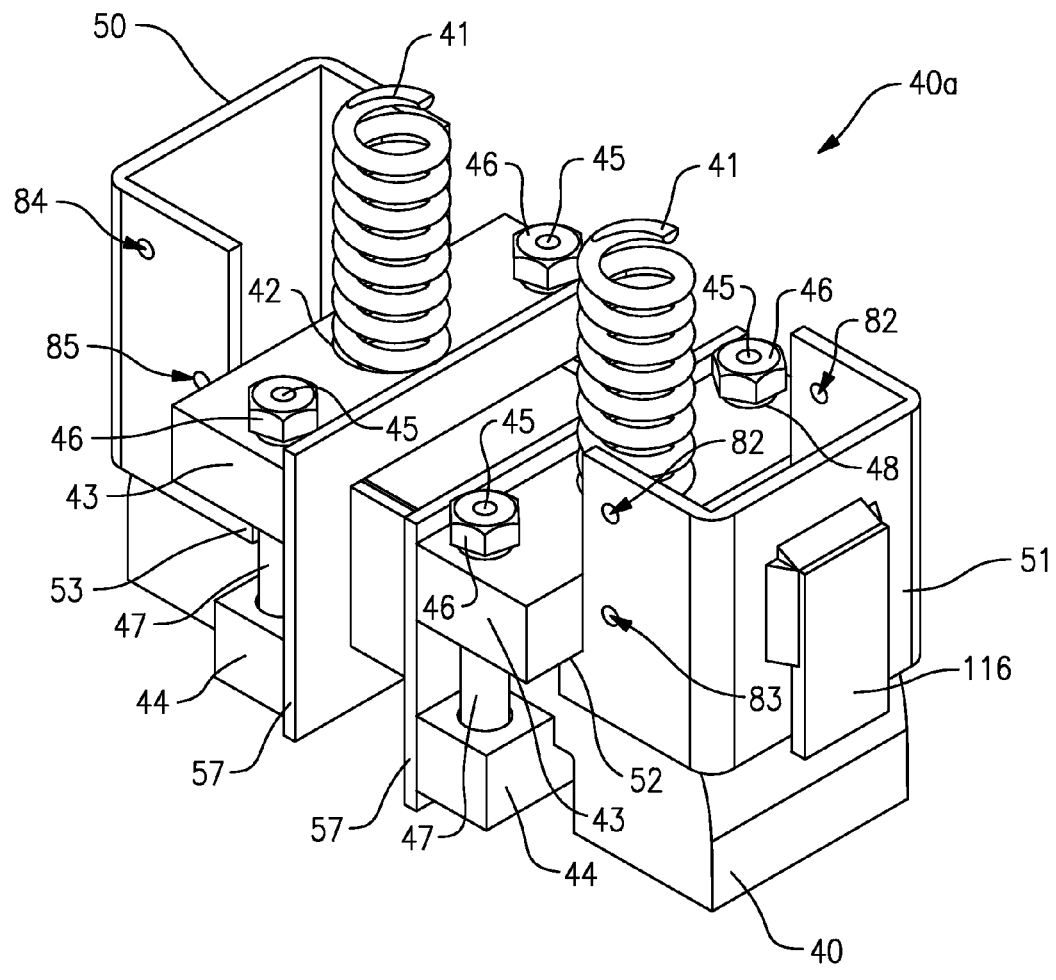
FIG. 7 illustrates an example upper magnetic core subassembly.
Figure 8:
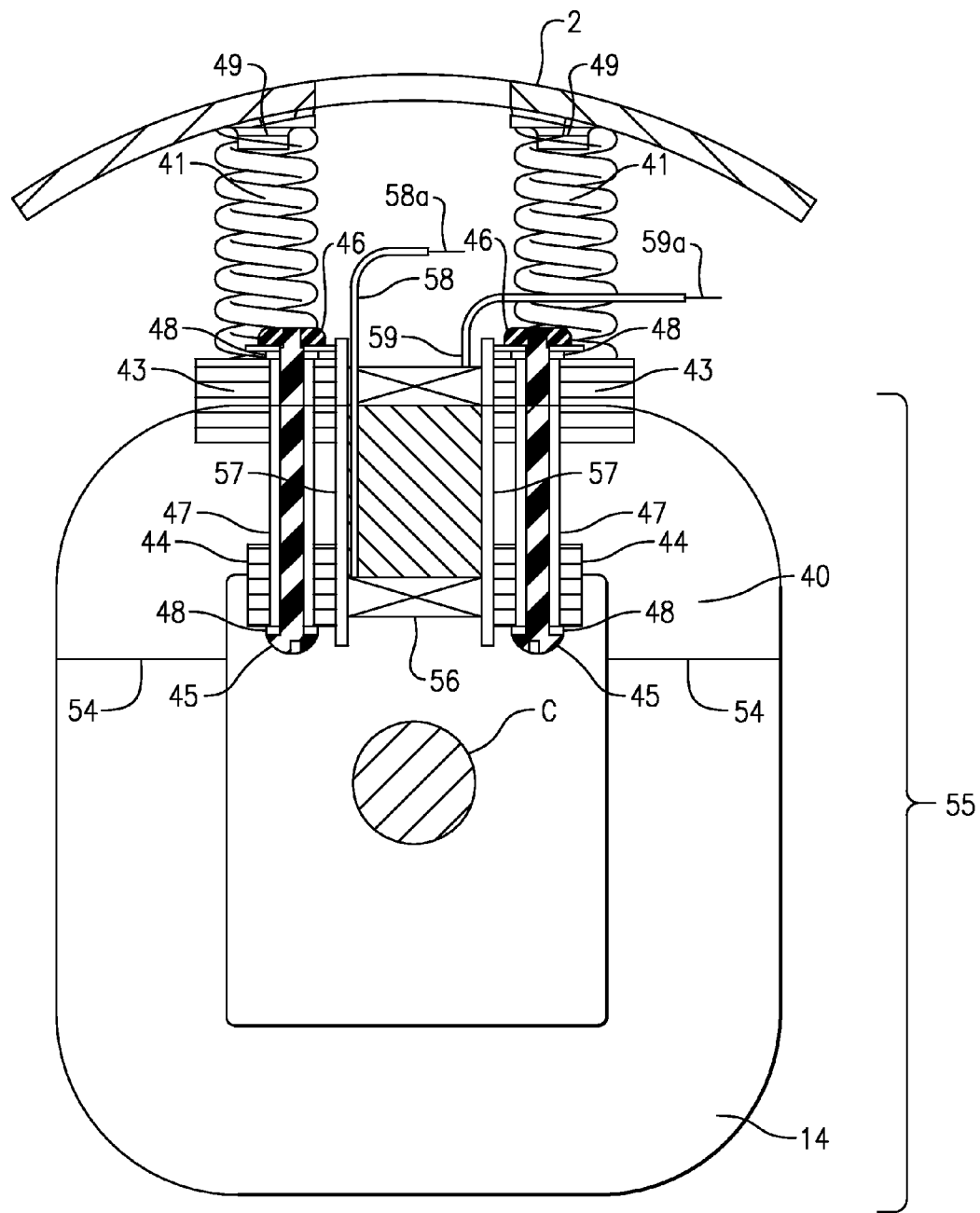
FIG. 8 illustrates an expanded view of an example upper magnetic core and an example lower magnetic core surrounding the conductor and an example power supply transformer.

FIGS. 7 and 8 illustrate the bottom of the compression springs 41 are held in alignment in two cylindrical pockets 42 of two identical horizontal upper core blocks 43 which are each used to clamp the upper magnetic core 40 to two identical magnetic horizontal lower core blocks 44. The top of the compression springs 41 are held in place with two projections 49 extending downward on the inside of the upper housing 2. The compression springs 41 are totally enclosed by the upper housing 2 and are protected from the adverse weather which can cause corrosion. The air gaps 54 between the upper and lower magnetic cores 40 and 14 are totally enclosed by the upper housing 2 which prevents the air gaps 54 from becoming corroded due to moisture from the environment. The horizontal upper core blocks 43 and the horizontal lower core blocks 44 are clamped around the upper magnetic core 40 on each side using two through bolts 45 and two nuts 46 in the front and two through bolts 45 and two nuts 46 located in the back of the upper horizontal core blocks 43 and horizontal lower core blocks 44.

When the two large compression springs 41 push the upper core blocks 43 down, the upper magnetic core 40 is prevented from falling out of a left core shoe 50 and a right core shoe 51, by a step 52 located at the bottom of the right core shoe 51 and a step 53 located at the bottom of the left core shoe 50.

When the lower magnetic core 14 mates with the upper magnetic core 40, the lead screw 22 can be turned further clockwise to move the two upper core blocks 43 away from the steps 52 and 53 and further compress the compression springs 41. The lead screw 22 can continue to be turned clockwise and compress the compression springs 41 until the lower jaw 7 and the upper jaws 6 are tight on the conductor C.

Electrical insulating spools 47 are inserted over each of the through bolts 45 and electrical insulating washers 48 are inserted under the head of each through bolt 45 and under each nut 46. The insulating spools 47 and the insulating washers 48 on each of the through bolts 45 prevent shorted electrically conductive paths around the upper magnetic core 40 which is comprised of the four through bolts 45, four nuts 46, the two electrically conductive upper core blocks 43 and the two lower core blocks 44.

When the upper jaws 6 and the lower jaw 7 are firmly tightened on the conductor C, the compression springs 41 are compressed to their maximum distance, and thus the maximum compressive force is also applied to the lower magnetic core 14 and the upper magnetic core 40. This decreases the size of the air gaps 54 between the lower magnetic core 14 and the upper magnetic core 40 and the magnetic reluctance between the lower magnetic core 14 and the upper magnetic core 40. Depending on the size of the conductor C, varying amounts torque can be applied to the hotstick driver assembly 9 to tighten the opening and closing mechanism 39 on the conductor C.

The physical size and shape of the upper jaws 6 and the lower jaw 7 are designed such that approximately the same compressive force is applied to the upper magnetic core 40 and the lower magnetic core 14. In one example, there are five different sets of upper and lower jaws 6 and 7 that can fit different conductor sizes and types ranging from 0.162 inches in diameter and up to 1.17 inches in diameter. The opening and closing mechanism 39 allows the STR unit 1 to be installed on a wide range of conductor diameters without changing the upper jaws 6 and the lower jaws 7 while maintaining sufficient contact between the upper magnetic core 40 and the lower magnetic core 14 to complete the magnetic circuit of the power supply transformer 55 of the STR unit 1 which derives its power from the current flowing through the conductor C to power a power supply module 60 of FIG. 9. Because the STR unit 1 derives power from the conductor C, batteries or solar cells are not required to power the STR unit 1. The STR unit 1 is powered at all times when current is flowing in the conductor C, even at current levels as low as 6.8 amperes and still process data and transmit data at 1 watt power levels because of the low threshold of the power supply module 60.

Maintaining a minimum magnetic reluctance insures that a power supply transformer 55 (FIGS. 8 and 9) will provide the needed secondary voltage $V_2$ and secondary current $I_2$ to operate the power supply transformer 55, sensor electronics module 63, and transmitter/receiver 64. The power supply transformer 55 includes the upper magnetic core 40, the lower magnetic core 14, and a coil winding 56. The upper magnetic core and the lower magnetic core form a window W for accepting the conductor C.

Figure 12:
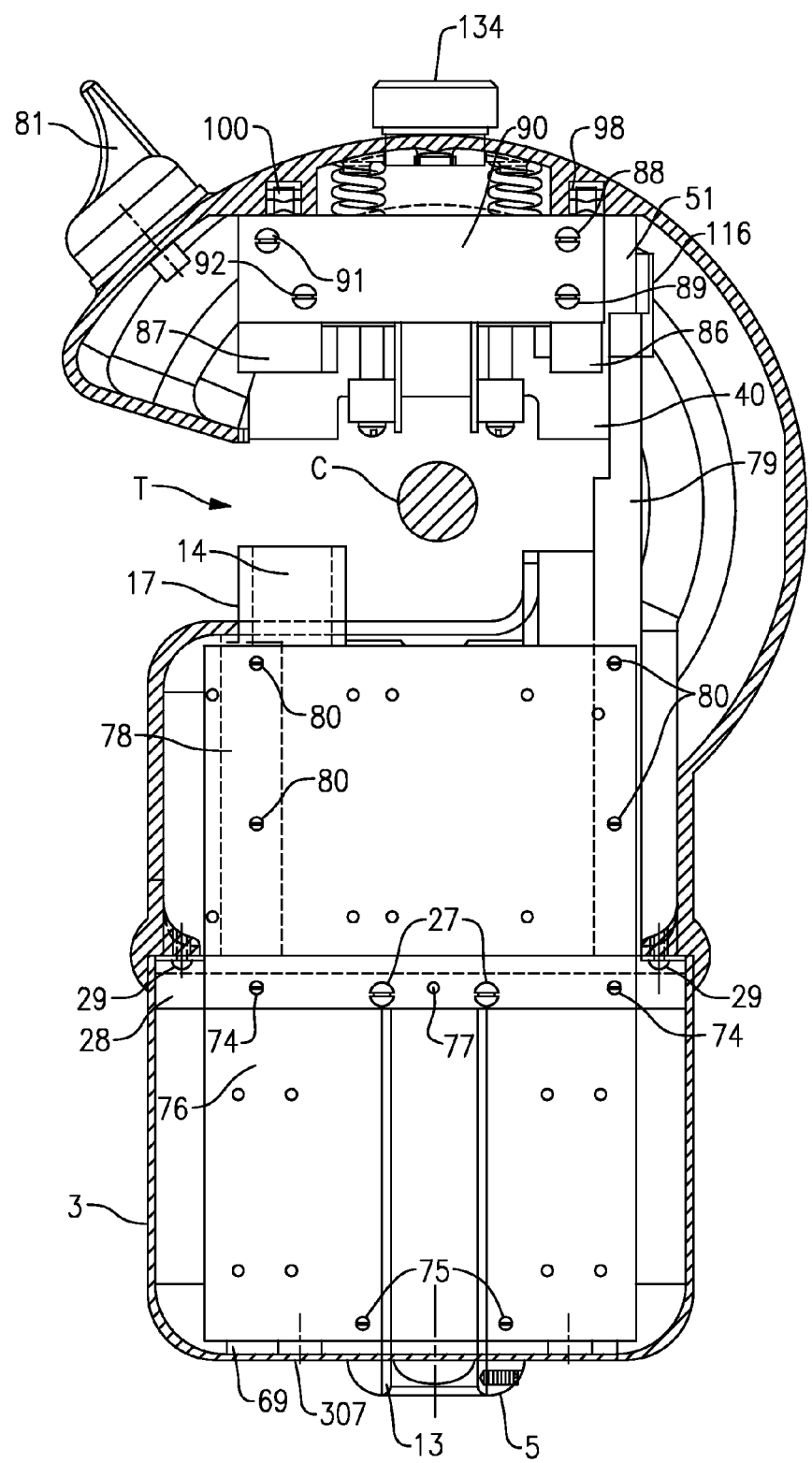
FIG. 12 illustrates a cross-sectional view taken along line B-B of FIG. 2.

The number of secondary turns $N_2$ of wire on the coil winding 56 are optimized to produce the required secondary voltage $V_2$ and secondary current $I_2$ with a minimum of current $I_1$ in the conductor C. The coil winding 56 is held in place by two coil bobbins 57 which are supported laterally by the two upper core blocks 43 and the two lower core blocks 44. Secondary leads 58a and 59a of coil windings 58 and 59, respectively, are connected to the power supply module 60 which maintains the same level of secondary voltage across leads 61 and 62 for the sensor electronics module 63 and the transmitter/receiver 64 even though the primary current may range from 34 amperes up to 1000 amperes. Lower primary currents of 6.8 amperes are achievable with the low threshold current power supply module 60. The power supply module 60 contains an energy storage device 256 (FIG. 13) which can power the transmitter/receiver 64 when the conductor C current ceases to flow. A transmitting and receiving antenna 81 for the on-board transmitter/receiver 64 is mounted on the upper housing 2 (FIG. 12).

Locating the coil winding 56, 58, and 59 on the upper magnetic core 40 allows the heat from the coil winding 56, 58, and 59 to escape through a vent 65 (FIG. 1) in the upper housing 2. When the conductor sensor S located within the STR unit 1 measures the temperature of the conductor C, it is important that the heat from the coil windings 56, 58, and 59 does not affect the temperature of the conductor C or the conductor temperature sensor S, which is in electrical communication with the sensor electronics module 63. As shown in FIG. 6, a thermally insulating barrier 66 located below the coil windings 56, 58, and 59, allows for a more accurate temperature reading of the conductor temperature by blocking heat from the coil windings 56, 58, and 59.

FIGS. 10-12 and 13 illustrate the lower magnetic core 14 with the lower core covers 17, the lead screw 22, the hotstick guide tube 13, and other related parts in both exploded and collapsed views. The hotstick guide tube 13 is anchored at the top with the through bolts 27 that extend through the bottom support 28 and the hotstick guide support 26. A round cylindrical milled slot 67 is located along opposing sides of the top of the hotstick guide tube 13 to accept the through bolts 27 that support the hotstick guide tube 13.

A central hole 70 extends through a base plate support 68 and a base plate 69 for accepting a bottom portion of the hotstick guide tube 13. The base plate support 68 and the base plate 69 are connected to each other with four identical threaded screws 71. The hotstick guide tube 13 is attached to the base plate support 68 and the base plate 69 with set screws 72 and 73. Left and right side panels 76 of FIG. 12 are attached to the base plate support 68 and the bottom support 28 for the lower core 14 with the use of two identical screws 74 extending through the bottom support 28 and the side panel 76 and at the bottom with two identical screws 75 extending through the side panel 76 and the base plate support 68.

The threaded bushing 25 rests on top of the hotstick guide tube 13 and is prevented from turning relative to the hotstick guide tube 13 using a set screw 77. The left and right side panels 76 not only provide added strength, but also provide the physical space to mount the power supply module 60, the transmitter/receiver 64, the sensor electronics 63, and support left and right lower core guides 78 and 79.

The left lower core guide 78 and a right lower core guide 79 are "U" shaped and guide the opening and closing mechanism 39 such that the lower magnetic core 14 is aligned with the upper magnetic core 40. Each of the left and right lower core guides 78 and 79 are attached to the left and right side panels 76 with four threaded screws 80. The lower housing 3 is placed over the hotstick guide tube 13 at the bottom and fitted up to the base plate 69 and held in place with the collar 5. This means that once the collar 5 is removed, the lower housing 3 can be removed thus allowing access to the power supply module 60, sensor electronics module 63, and the transmitter/receiver 64 of FIG. 9 mounted inside and on the left and right side panels 76 for easy maintenance and repair.

FIGS. 7 and 12-15 illustrate an upper magnetic core subassembly 40a mounted to the upper housing 2. The left and right core shoes 50 and 51 support the upper magnetic core 40 such that the upper magnetic core 40 can move freely up and down inside the left and right shoes 50 and 51. The left and right core shoes 50 and 51 are attached to the upper housing 2 using four support blocks 86 and 87 of FIG. 14, right and left upper core guides 90 and 93, and four vertical through bolts 94, 95, 96, and 97.

Figure 13:
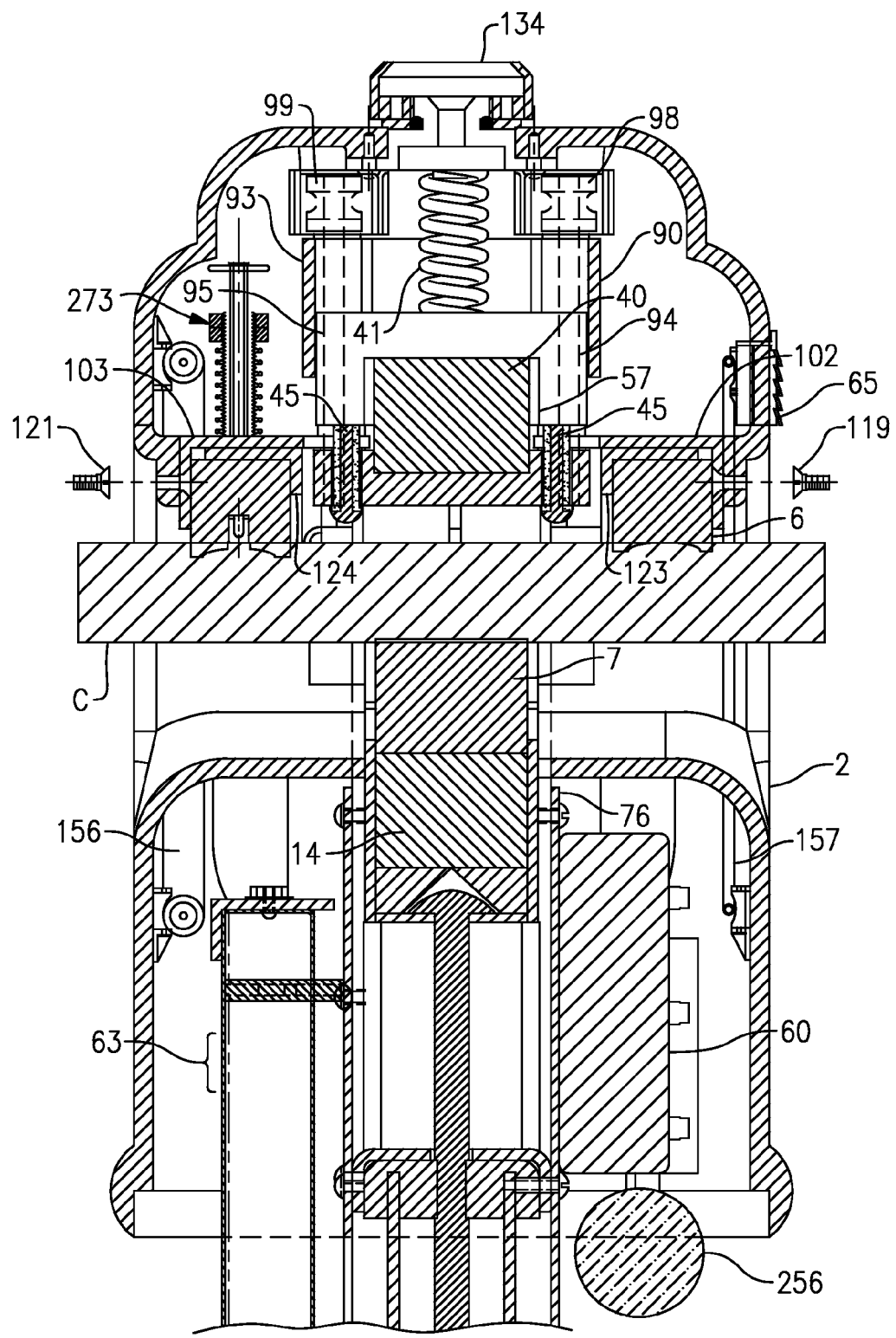
FIG. 13 illustrates a cross-sectional view taken along line C-C of FIG. 1.
Figure 16:
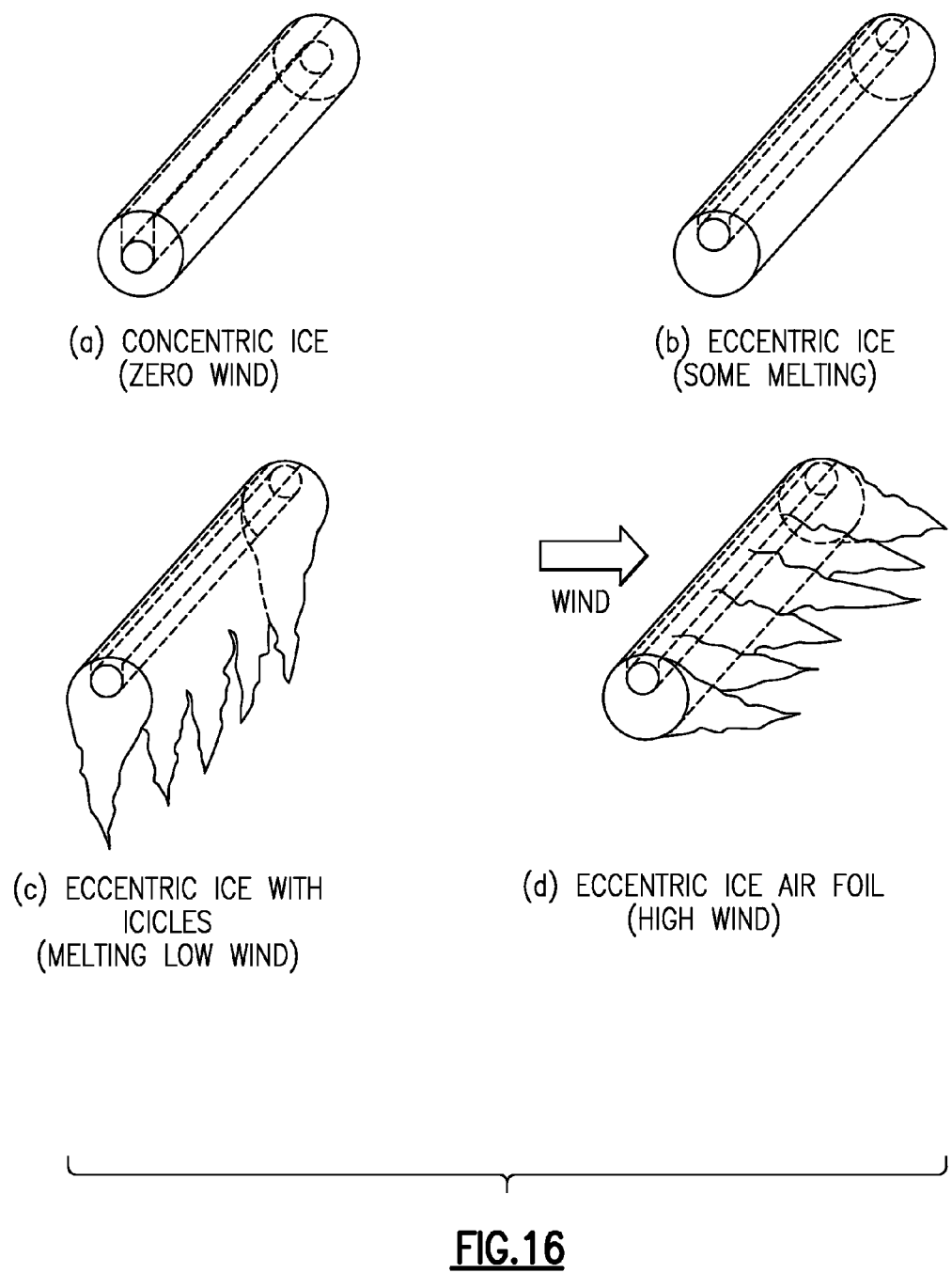
FIG. 16 illustrates typical ice formation shapes.

The upper magnetic core subassembly 40a can be inserted through the throat T and fastened to the inside of the upper housing 2. A top portion of the upper housing 2 is "C" shaped which provides a surface on the inside for mounting a current sensing device 156 for measuring the power line frequency current (60 Hz or 50 Hz) and a loop coil 157 for measuring lightning stroke current (FIGS. 13 and 16).

The right core shoe 51 has two identical threaded holes 82 and 83 on the front and back for a total of four, and left core shoe 50 has two identical threaded holes 84 and 85 on the front and back for a total of four as shown in FIGS. 7 and 14. As shown in FIG. 14, two identical support blocks 86 on the right side are placed on the front and back of the right core shoe 51 and two identical support blocks 87 are placed on the front and back of the left core shoe 50.

To align the two right side support blocks 86 with the two sets of threaded holes 82 and 83 on the right side of the right core shoe 51, threaded screws 88 and 89 are first inserted into the upper and lower holes in the right side upper core guide 90 and then through the two holes in the right support block 86 and screwed into the accommodating threaded holes 82 and 83 of the right core shoe 51. The two left side support blocks 87 are held in alignment with the left core shoe 50 by first inserting two threaded screws 91 and 92 through the other end of the right side upper core guide 90 and then through the holes in the left side support block 87 and screwed into the threaded holes 84 and 85 of the left core shoe 50. The same process is repeated on the back side by connecting support blocks 86 and 87 to the left upper core guide 93 with the backside of the right core shoe 51 and the back side of the left core shoe 50.

The purpose of the upper core guides 90 and 93 is to insure the two long vertical through bolts 94 and 95 placed through the vertical holes in the two right side support blocks 86 and two long vertical through bolts 96 and 97 placed through the vertical holes in the two left side support blocks 87 line up with the four threaded holes in four threaded inserts 98, 99, 100, and 101, which are embedded in the casting of the upper housing 2. The two right side support blocks 86 are prevented from falling down by inserting the back of a right side upper jaw holder 102 and the back of the left side upper jaw holder 103 over the vertical through bolts 94 and 95 and threading nuts 104 and 105 onto the two vertical through bolts 94 and 95 and tightening them down, respectively. The two left side support blocks 87 are held in place by inserting the vertical through bolts 96 and 97 through the front hole in the right side upper jaw holder 102 and the front hole in the left side upper jaw holder 103 and threading two nuts 106 and 107 on the vertical through bolts 96 and 97 and tightening them down, respectively.

Four threaded through standoffs 108, 109, 110, and 111 are screwed onto the four vertical through bolts 94, 95, 96, and 97, respectively. The thermal barrier 66 is placed over the four bottom holes of the standoffs 108, 109, 110, and 111 and screwed to the standoffs 110 and 111 on the front left side with two flat head screws 112 as shown in FIG. 15.

Figure 15:
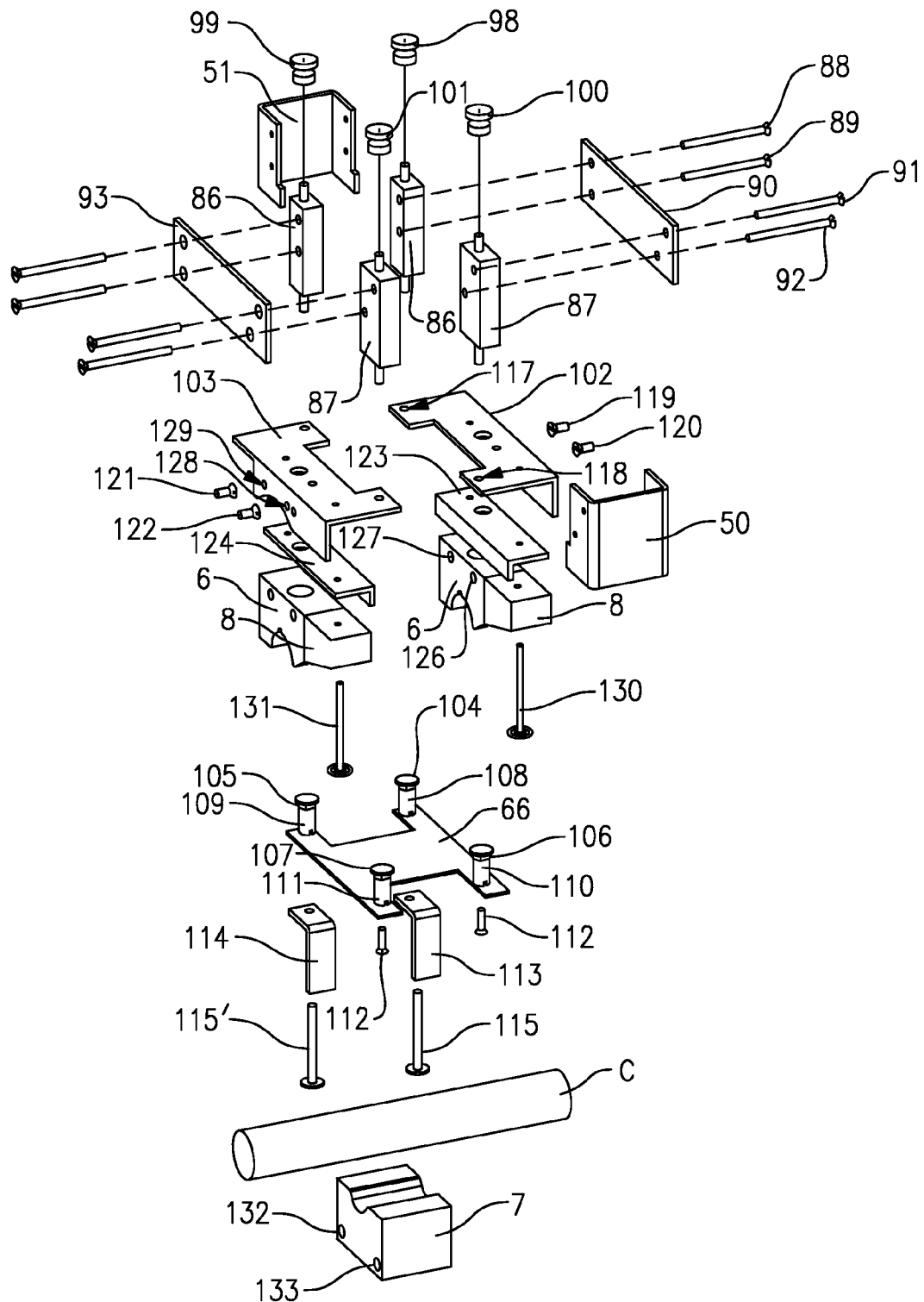
FIG. 15 illustrates an exploded view of an upper magnetic core mount and the upper and lower jaws.

FIGS. 2 and 15 illustrate casting fillers 113 and 114 located on the back left and back right sides of the STR unit 1 and secured with round head screws 115 which are first inserted through holes in the casting fillers 113 and 114 and then through the two back holes on the right and left side of the thermal barrier 66 and into the standoffs 108 and 109, respectively.

After the upper magnetic core subassembly 40a is mounted, the left and right lower core guides 78 and 79 including the opening and closing mechanism subassembly 39 and the left and right side panels 76 are inserted through the bottom of the upper housing 2 (See FIG. 12). Four screws 29 are inserted through the two holes on the left and the two holes on the right of the bottom support 28 and screwed into the threaded holes of the upper housing 2. It should be noted that during the insertion process, the right lower core guide 79, shown in FIG. 12, slides around the outside surface of the right core shoe 51 and underneath a tab 116 at the top as a weldment on the right upper side of the right core shoe 51.

As shown in FIG. 12, the tab 116 insures that the right lower core guide 79 fits precisely around the outside of the right core shoe 51 to provide a near perfect alignment of the lower magnetic core 14 with the upper magnetic core 40. The precise alignment between the upper magnetic core 40 and the lower magnetic core 14 reduces magnetic reluctance by decreasing the air gaps 54. This results in a decrease in the threshold current for the operation of the power supply module 60.

Referring to FIGS. 14 and 15, the right side upper jaw holder 102 and the left side upper jaw holder 103 support the two upper jaws 6 and the jaw inserts 8. The long vertical through bolts 96 and 97 which are screwed into the threaded inserts 100 and 101 at the top and on the inside of the upper housing 2 fit through top holes 117 and 118 on the back and front of the right side upper jaw holder 102 on the right side. Also, flush mount screws 119 and 120 are inserted on the back and through corresponding holes in the right side upper jaw holder 102 and are screwed into the upper housing. The flush mount screws 119 and 120 are installed before the upper jaws 6 and inserts 8 are mounted to the right side upper jaw holder 102. The same arrangement for mounting the left side upper jaw holder 103 is followed using screws 121 and 122.

Right and left upper jaw keepers 123 and 124 prevent the upper jaws 6 from dropping down on the inside, because spring pins 126 and 127 are located on the outside and when depressed snap into the holes 128 and 129 of the right side upper jaw holder 102. The same procedure is followed with the left upper jaw keeper 124.

The jaw inserts 8 on the right and left sides of the STR unit 1 and in front of the upper jaws 6 are held in place by inserting threaded bolts 130 and 131 into each insert 8 and through the right and left keepers 123 and 124 and screwing into the upper jaw holders 102 and 103. The spring pins 132 and 133 are included in the lower jaw 7 which when depressed snap into the two holes 15 in the lower jaw holder 16.

Figure 9:
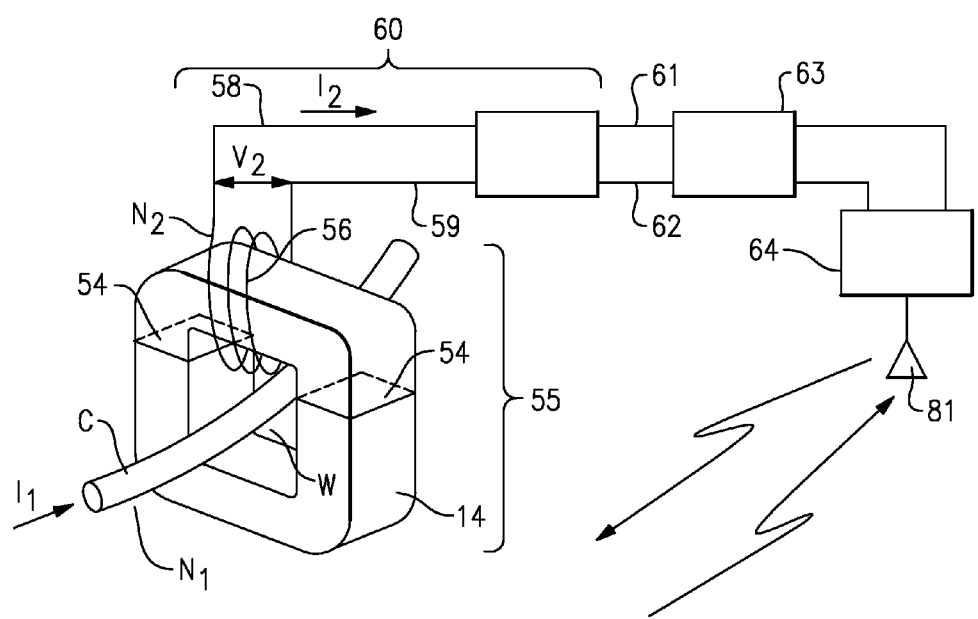
FIG. 9 illustrates a schematic view of the line mounted power supply, electronics and transmitter-receiver of the STR unit.

The transmitting and receiving antenna 81 for the on-board transmitter/receiver 64 shown in FIG. 9 is mounted on the housing 2. The antenna 81 is displayed in FIGS. 1 and 2 and is installed on the top left side in FIG. 1. A solar sensor assembly 134 is located at the top of this housing and on its vertical centerline (FIG. 13). The small hole 140 located directly to the right of the conductor 1 allows access and adjustment of the electric power line sag sensor 140 (FIG. 1).

Ice can form in different shapes on electric power line conductors C. FIG. 16 shows four different ice formation shapes which are commonly encountered on line conductors C. The shape (a) of FIG. 16 is called concentric ice because the ice thickness is nearly the same around the circumference of the conductor C. This shape occurs during very low wind and light freezing rain conditions. It should be noted in (a) there are two vertical dotted lines shown, one on each side of the surface of the conductor C, and extend to the surface of the ice on top of the conductor C. The ice thickness sensor only needs to measure the thickness near the top of the conductor C, because it is necessary to only melt the ice in the region defined by the vertical slot directly above the conductor C by passing a higher magnitude of current (I) through the conductor C than was present during the ice formation process and heating up the conductor C over time. When the ice in this slotted region is nearly melted with this higher level of current then the weight of the remaining ice will cause this ice to drop off the line conductor C. The shape (b) of FIG. 16 is called eccentric ice which is offset vertically down from the horizontal centerline of the conductor C. Here again, it is only necessary to melt most of the ice directly above the conductor C by increasing the current in the line which causes higher $I^2R$ losses or heating of the line. Ice shape (c) of FIG. 16 is formed when some of the ice has melted causing icicles, but here again the only ice thickness that needs to be measured is that directly above the conductor C. The presence of the icicles on the bottom has little effect on the amount of current and time needed to melt the required ice. The last ice shape (d) of FIG.

16 is called eccentric ice with an air foil which is formed during high wind and freezing rain. Again, measuring the ice on top of the conductor C is required by the sensor to determine the level of current and time it will take to de-ice the line. There are two important conclusions to be drawn by this discussion. First, the sensor must not be mounted on the STR unit 1 directly above the conductor C and must be mounted far enough away in a lateral direction from the STR unit 1 to not interfere with the ice formation process. Second, the sensor must be mounted on the STR unit 1 such that it can still measure the thickness of the ice on top of the conductor C. Therefore, it can be mounted at an angle measured from the vertical centerline of the conductor C downward which avoids interfering with the ice formation, but still measures the ice thickness above the conductor C at the edge of the slot of ice to be melted.

The STR unit 1 includes a hollow sphere 365 having a laser for measuring distance to and ice thickness of the conductor C. The hollow sphere 365 is mounted away from the conductor C and attached to the upper housing 2 with the corona free tubular standoff bracket 366 shown in a front view of the STR unit 1 in FIGS. 17, 24, and 25.

Figure 17:
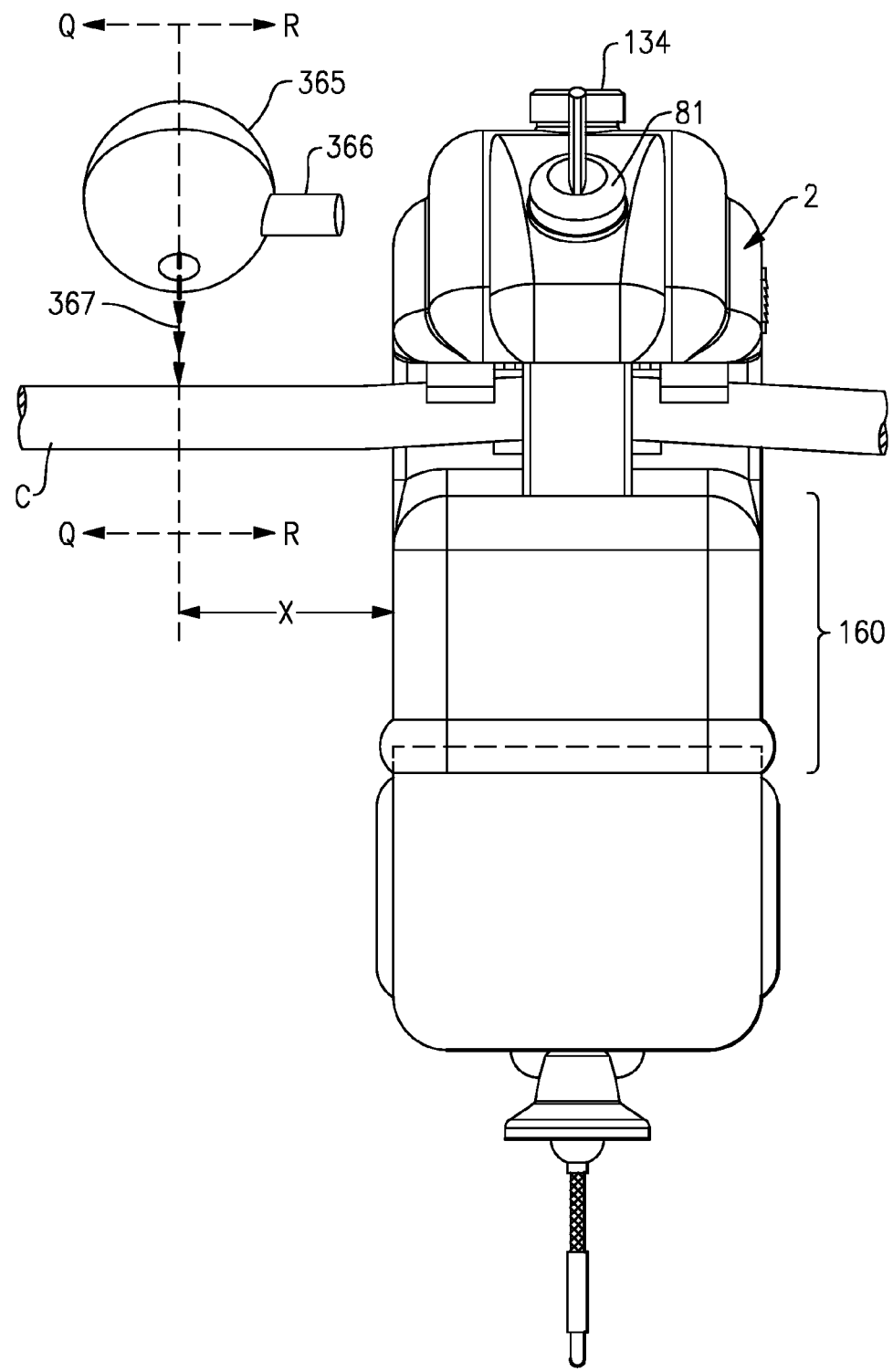
FIG. 17 illustrates a front view of the STR unit installed on the conductor with an ice thickness sensor.
Figure 18:
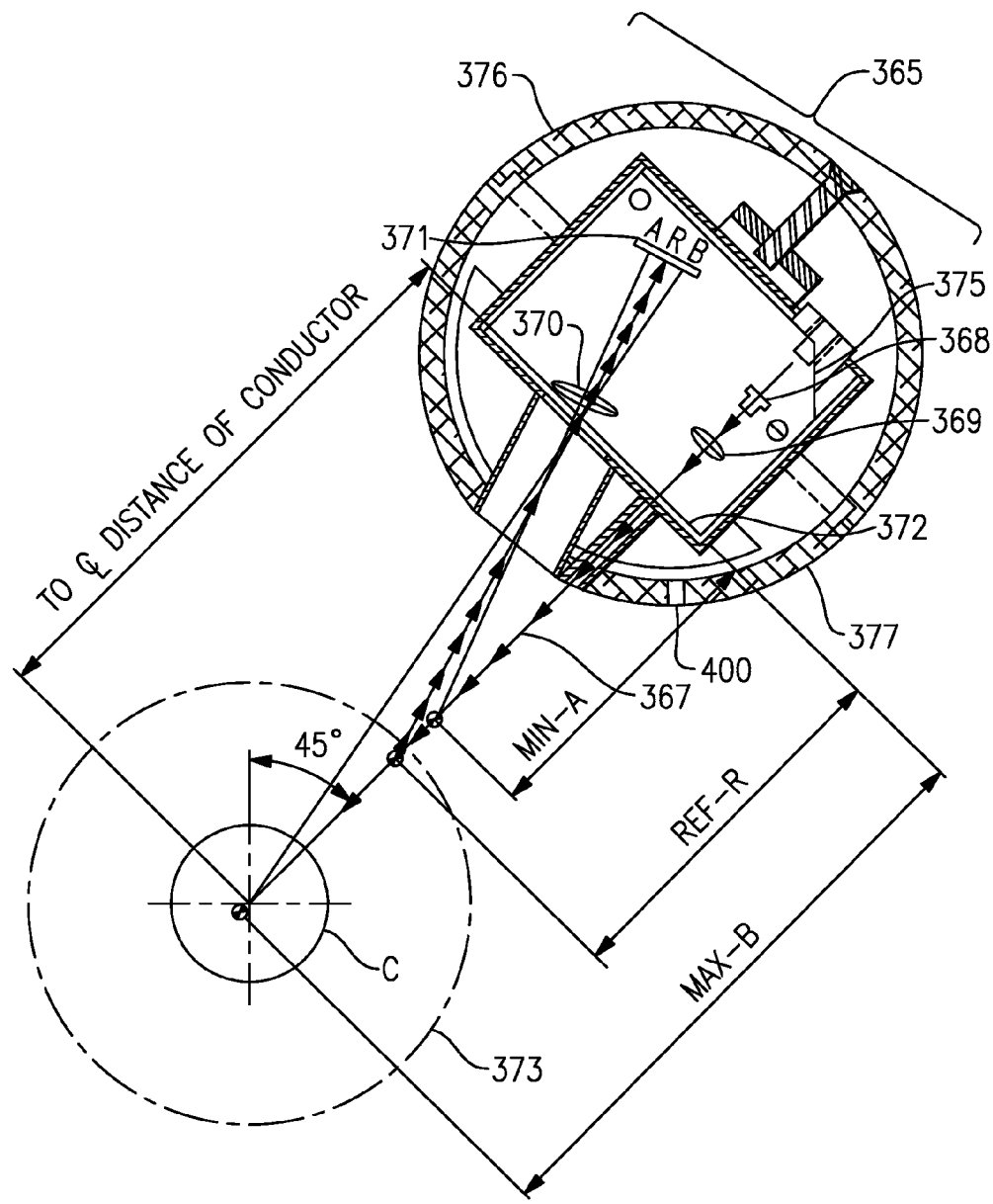
FIG. 18 illustrates a cross-sectional view taken along line Q-Q of FIG. 17 showing reference, maximum, and minimum measuring distances of a laser.

FIG. 18 illustrates a cross-sectional view taken along line Q-Q of FIG. 17. The hollow sphere 365 is located at an angle as measured from the vertical centerline of the electric power line conductor C to an emitter beam 367 of the laser. In one example, the lower surface of the hollow sphere 365 is mounted 6.47 inches (164.3 mm) from the surface of the largest conductor C and at an angle of 30 degrees from the vertical. This location minimizes the effect on the formation of the ice on the conductor C even if the radial thickness of ice was approximately 1.00 inch during freezing rain (almost vertical downward) with light wind conditions. Furthermore, the location of the hollow sphere 365 has little effect on the ice formation process with heavy winds and rain approaching from the left side or the right side of the conductor C. An angle of 30 degrees as measured from the vertical to the emitter beam 367 of the laser allows for measurement of ice thickness, because it is helpful to know the thickness of ice in the slotted region above the conductor C to determine the current and time necessary to thaw the ice. (See FIG. 20). Also this location of the hollow sphere 365 has little effect of the height of the hollow sphere 365 effecting the solar radiation measurements from the solar sensor assembly 134 located on the top of the STR unit 1 of FIG. 17.

Figure 19:
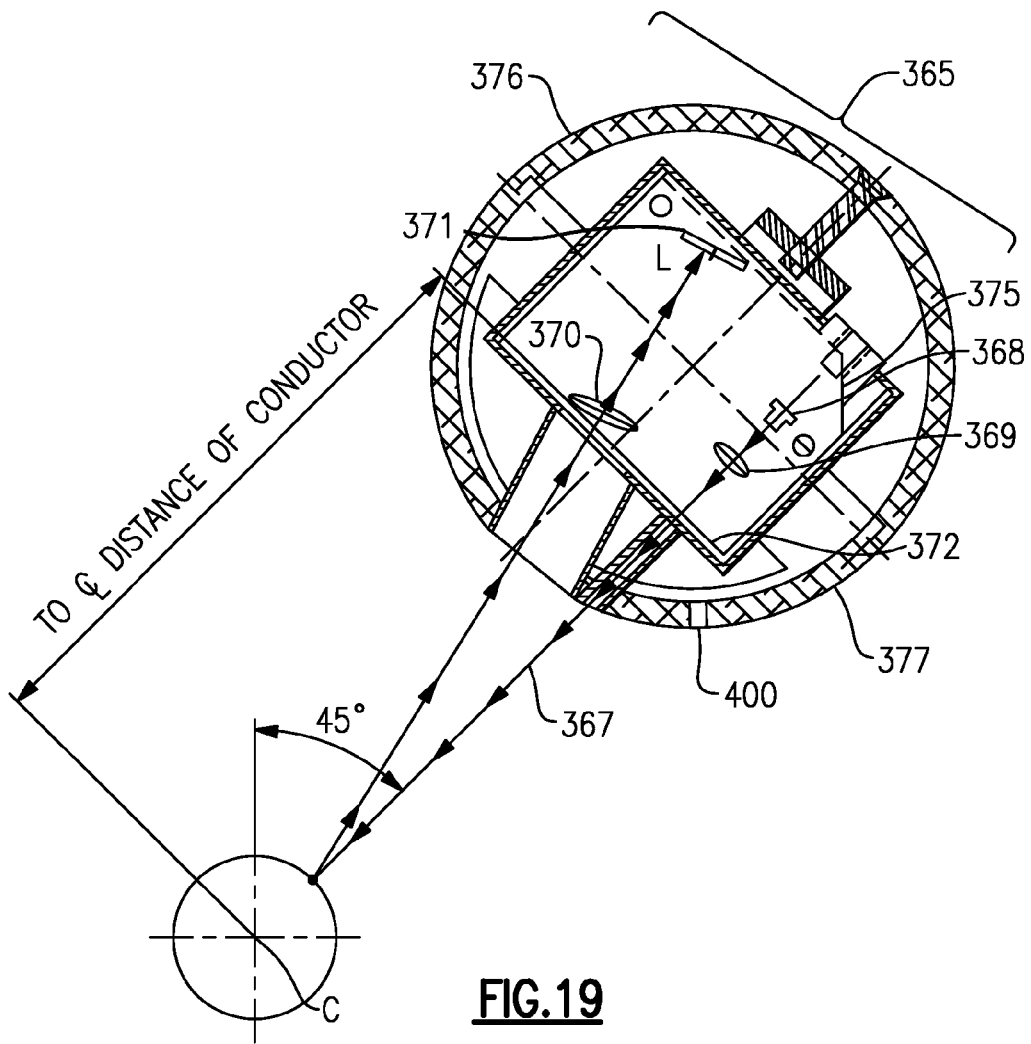
FIG. 19 illustrates a cross-sectional view taken along line Q-Q of FIG. 17 showing distance measurements to a large diameter conductor (L).
Figure 20:
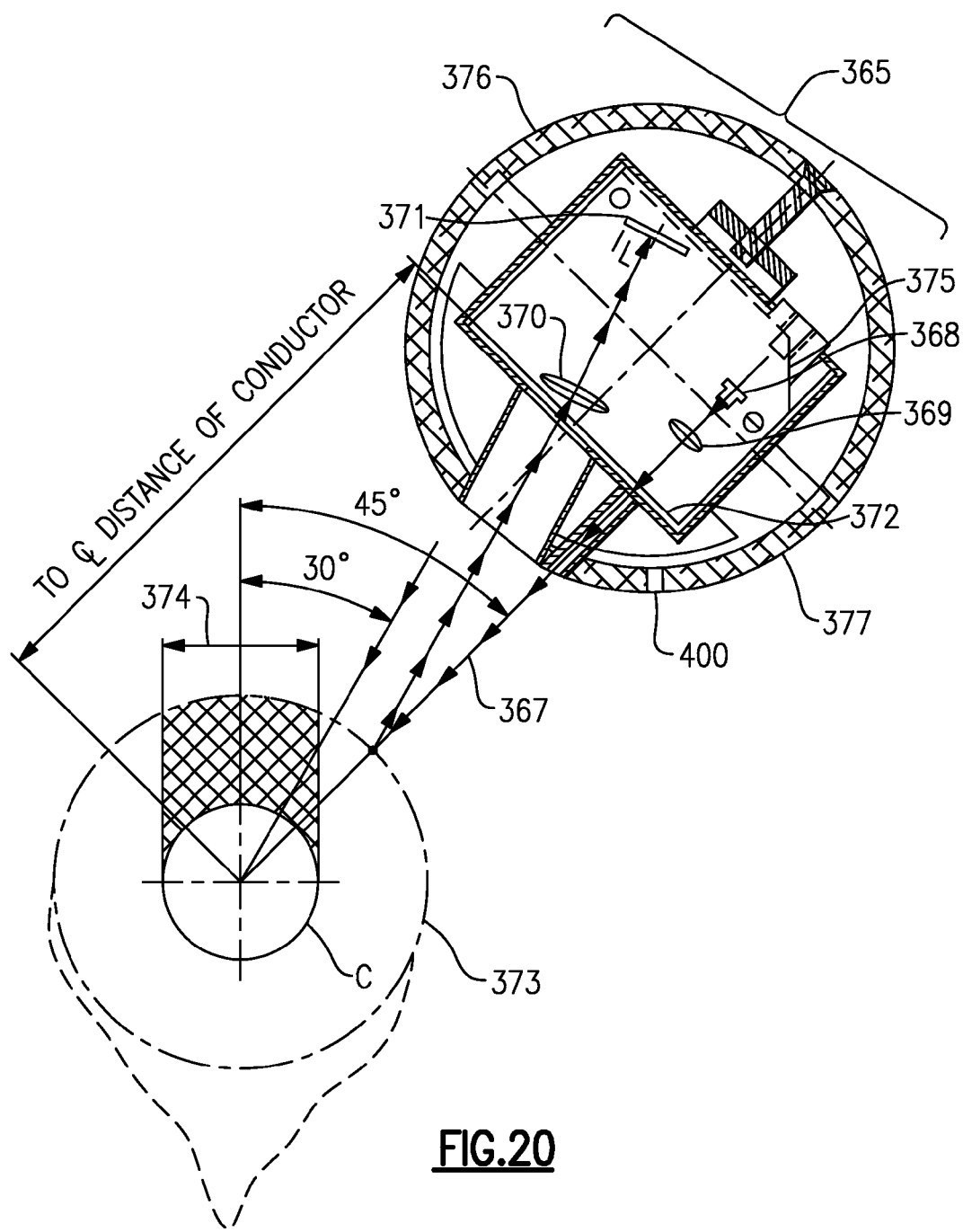
FIG. 20 illustrates a cross-sectional view taken along line Q-Q of FIG. 17 showing distance measurements to 1.00 inch radial ice thickness on the large conductor (L).
Figure 21:
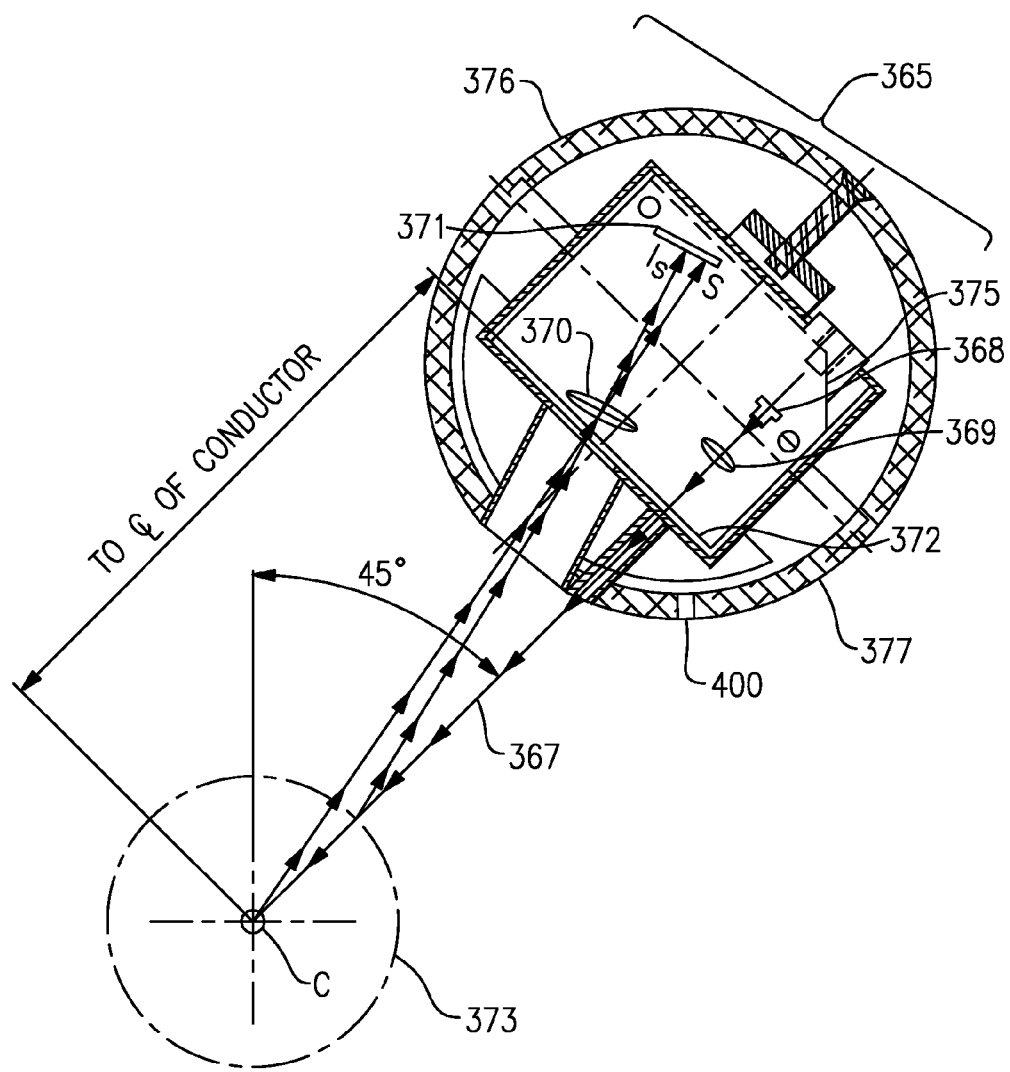
FIG. 21 illustrates a cross-sectional view taken along line Q-Q of FIG. 17 showing distance measurements to a small diameter conductor (S) and to 1.00 inch radial ice thickness on the smallest conductor (S).

The relative distances between the bottom of the laser head 372 and the largest and smallest conductors for 1.00 inch (25.4 mm) of radial ice shown in FIG. 18 and those that follow, namely FIGS. 19-21 are for illustrative purposes only and do not represent the actual distances the laser must be positioned to not affect the ice buildup. The actual distances are far greater than those shown on FIGS. 19-21.

The principle of operation of the laser triangulation begins with the red semi-conductor laser light source 368 shown in FIG. 18. The laser light source 368 emits a laser beam called the emitter beam 367 which is focused with a transmitter lens 369 onto a target, such as the conductor C or ice formed over the conductor C. The light reflected off the target is focused by a receiver lens 370 and forms an image on a light sensitive receiving element 371.

If the target changes its position, for example if ice begins to form on the surface of the conductor C, then the position of the reflected spot of focused light on the light sensitive receiving element 371 will change. The signal conditioning electronics of the laser detects the spot position on the light sensitive receiving element 371 and provides a digital or analog output signal proportional to a position of the target. In FIG. 18, the reference distance "REF-R" to the target appears as "R" at the center of the light sensitive receiving element 371, the minimum distance "MIN-A" to the target appears as "A," and the maximum distance "MAX-B" to the target appears as "B" on the light sensitive receiving element 371, respectively.

The maximum distance the laser needs to measure MAX-B must be slightly greater than the distance from the bottom of the laser head 372 to the centerline of the conductor C so as to measure the distance to small conductors C and the minimum distance that needs to be measured must be less than the distance from the bottom of the laser head 372 to the maximum buildup of 1.00 inch of ice 373 on the largest conductor.

In another example, the light sensitive receiving element 371 shown in FIG. 18 could include older technology, such as PSD (position sensitive device), or CMOS, or CCD (charged coupled device). An important element of the laser triangulation sensor for ice thickness measurement is the light sensitive receiving element 371. The PSD triangulation has been used for about 30 years, however the repeatability of the PSD receiver is affected by a number of variations in the type of target being measured. If the surface condition of the target changes, or if the target texture changes, or if the tilt of the target changes, this will change the shape of the light spot on the receiving element which alters the center of the light distribution and the output of the PSD element will change. Also, if the light intensity changes with a change in target color while the spot position remains the same this will change the output. Therefore, the PSD technology cannot be used to measure the distance to the conductor C and measure the thickness of ice on the conductor C for the following reasons. First, new conductors C can have almost a mirror like finish with very little copper or aluminum oxide on their surfaces, however as they age their surfaces become blackened. Second, small diameter conductors C may have smooth cylindrical surfaces, but large conductors C have surfaces containing small strands of wire wrapped in the form of a helix which allows the conductor to be more flexible. Third, ice formations may have air entrained bubbles, frozen snow or frost, or be almost as clear as glass. In the former, the light beam may be reflected off the surface, but in the latter the light beam will become diffused within the clear ice and less than 4 percent of the light is reflected back to the receiver.

The CCD laser can respond to changing surface conditions and achieve accurate measurements regardless of surface color and changes in surface texture. The CCD laser can provide accurate measurements with as little as one percent diffuse reflectivity therefore aged blackened conductors or new shiny surface conductors are no longer a problem. The CCD receiver element includes a pixel array and the light intensity distribution of the spot received is processed into a linear triangulation measurement. Also, a closed loop gain control is used to adjust the power output of the transmitting laser, based on the amount of reflected light received from the conductor C or ice 373. Such a CCD light sensitive receiving element 371 is used in the ice thickness measuring sensor shown in FIG. 18. The CCD dynamic range of sensitivity for the light sensitive receiving element 371 is between 800:1 and 1000:1 and the dynamic range of sensitivity for the CMOS receiver elements are typically only 200:1. Therefore CMOS lasers cannot, in general, be used to measure the ice thickness of all types of ice formations including clear ice.

A laser distance measuring sensor 375 used within the STR unit 1 includes the red semi-conductor laser 368 with a wavelength of 650 nm which has a light source output of 5 mW or greater and a wide beam spot diameter at reference to overcome measurement errors due to conductor stranding or small conductors at a considerable distance from the bottom of laser head 372. The laser distance measuring sensor 375 is powered by the onboard power supply module 60 (shown in FIG. 9) with a 12 Vdc source and the sensor electronics module 63 provides signal outputs from 0 to 5 volts dc corresponding to maximum and minimum measuring distances.

The sampling rate of the laser distance measuring sensor 375 can be ranged and the accuracy is typically 0.020 to 0.050 inches or less within an ambient temperature range of −30° C. (−22° F.) to +50° C. (122° F.). Also the laser distance measuring sensor 375 can withstand the Aeolian vibration up to 9.8 g of gravity from the conductor C due to the wind flowing over the conductor C and can operate successfully and within the stated measurement accuracy up to 6600 foot elevations above sea level.

As mentioned above, the drawings of FIGS. 19-21 are for illustrative purposes only. FIGS. 19-21 show the distance measurements to the following targets: (a) to the largest smooth diameter conductor (1.10 inches) denoted as 'L' on the light sensitive receiving element 371 of FIG. 19, (b) to the 1.00 inch of radial ice on the largest smooth conductor denoted as $I_L$ of FIG. 20, (c) to the smallest ('S') smooth conductor (0.162 inches), and (d) to the 1.00 inch of radial ice on the smallest smooth conductor ($I_S$) of FIG. 21.

To accurately measure the outside diameter of the conductor C and thickness of ice formed on the surface of the conductor C, the emitter beam 367 as shown in FIG. 18 must be pointed in a direction that goes through the center of the conductor C. Therefore, the emitter beam 367 must be impinging on the surface of the smooth circular conductor C at 90° or perpendicular to the surface of the conductor C.

Laser triangulation sensors can be used on highly reflective or mirror like surfaces like aluminum or copper conductors commonly referred to as specular. With these type surfaces the diffuse type laser which directs its emitter beam at 90° to the surface cannot be used because the light will be reflected directly back to the emitter. In these cases it is necessary to tilt the emitter beam 367 at a slight angle generally less than 2 degrees and the beam will now reflect back from the target at an equal but opposite angle and be focused onto the light sensitive receiving element 371.

For ideal performance, the target should be positioned normal or 90 degrees to the laser head emitter beam 367 to prevent errors in the distance measurement. The effect of the tilt angle is dependent on the target surface's reflective properties. For mirror like surfaces such as new power line conductors C, there may be small errors in the measurement if the tilt angle is changed by as much as 1 to 2 degrees. Laser sensors can be used to measure curved targets like the conductor C, but the beam should be positioned to the center of the curvature. Also, the laser head 375 should be oriented such that the curved surface does not skew the laser triangulation angle. Furthermore, the laser return light should not be blocked by some feature on the target surface.

Figure 22:
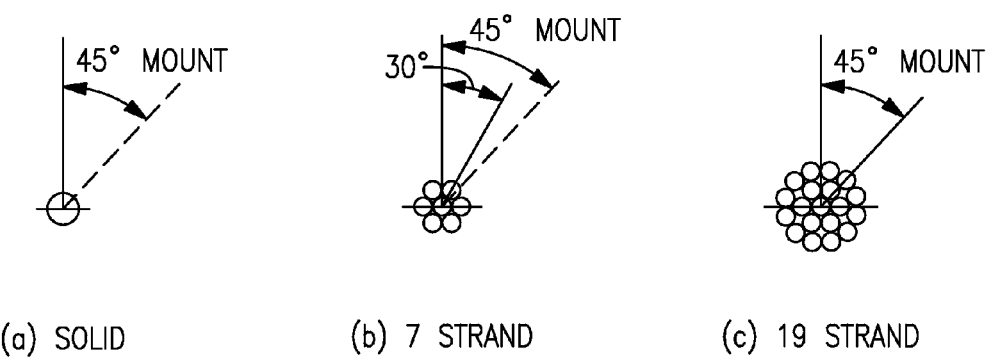
FIG. 22a-e illustrates typical all copper and all aluminum solid and stranded conductors.

As was stated earlier most power line conductors C are made up of strands of wire formed in a helix. Some typical examples of all copper and all aluminum solid and stranded conductors are shown in FIG. 22. If the emitter beam 367 is directed toward the center of the conductor C in each of these cases at an angle of 45° from the vertical, then the laser return light may be blocked in the 7 strand (b) and the 61 strand (e) cases. For the 61 strand (e) case, the return light may be trapped between the two strands appearing on each side of the 45° emitter light angle. If the emitter beam 367 is directed at an angle of 30 degrees for the 7 strand case and 37 degrees for the 61 strand case, the emitter beam 367 would be reflected back to the light sensitive receiving element 371, because the emitter beam 367 would strike the surface of the strand at an angle of 90° to its surface.

Figure 23:
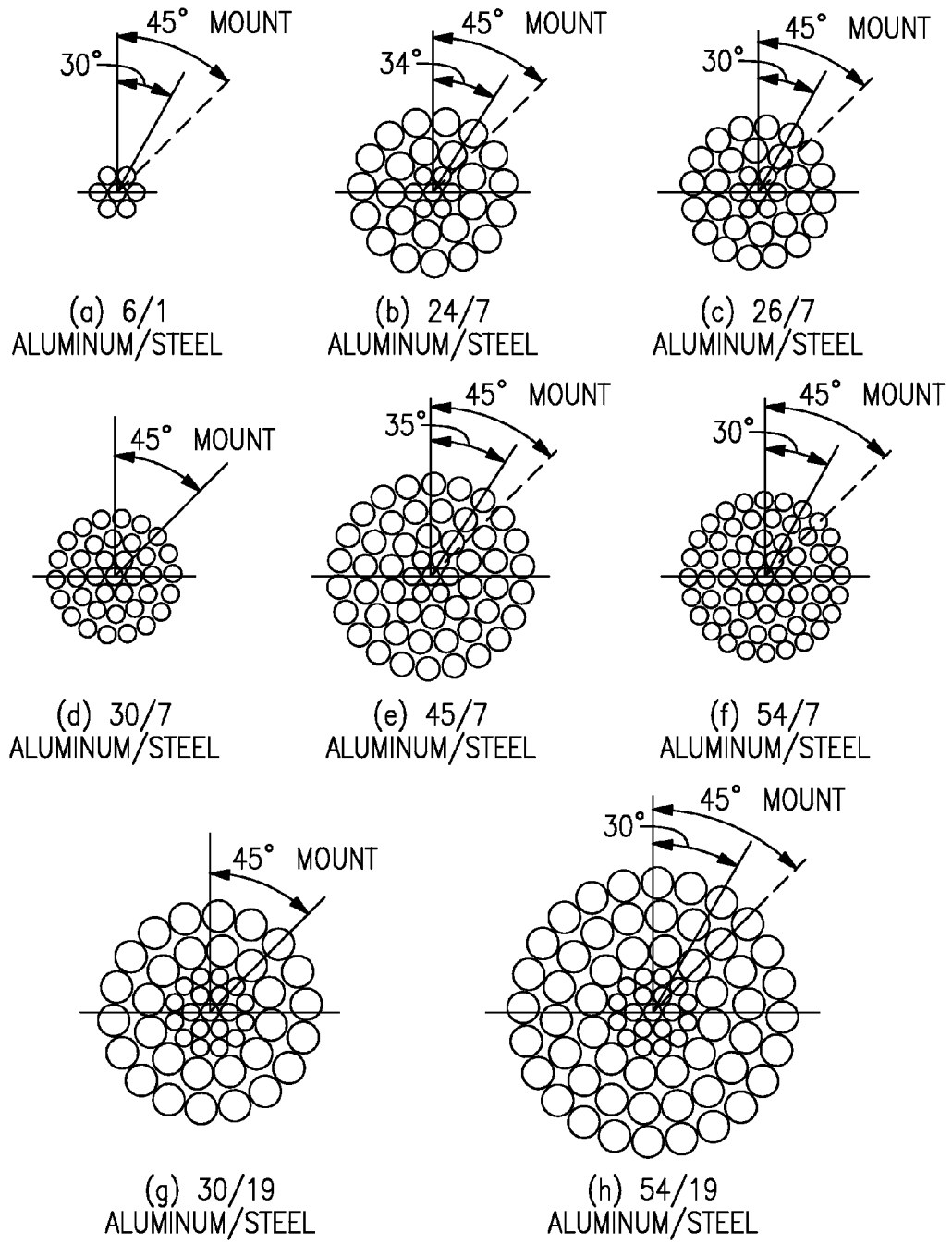
FIG. 23 illustrates typical ACSR stranded conductors.

Conductors C may include ACSR (aluminum conductor steel re-enforced) type conductors. Some typical types are given in FIG. 23. If the emitter beam 367 is positioned at 45 degrees to the vertical centerline of each conductor C, the 24/7 stranding (b), the 26/7 stranding (c), and the 45/7 stranding (e) conductors may block the return emitted beam 367. However, if the bottom of the laser head 372 is positioned such that the emitter beams 367 are directed at an angle of 30 degrees from the vertical centerline of the conductor C, blockage may not occur, and the reflected emitter beams 367 will be received by the light sensitive receiving element 371. For this reason the laser head 375 can be mounted to the upper housing 2 of FIG. 24 using the standoff bracket 366 at a 30 degree angle as measured from the vertical to the emitter beam 367.

If the emitter beam 367 is directed toward the centerline of the conductor C and 1.00 inch of radial ice 373 is formed over the largest conductor C of FIG. 20, the emitter beam 367 is still measuring the thickness of ice outside the ice notch width 374 (ice to be melted). Any slight errors in measurements due to the strand diameter, and partial blockages are overcome using a wide beam spot diameter at reference of at least 1.7 mm and spatial averaging with the CCD receiver element output data.

With the above explanation of the specific characteristics of the laser head 375 and the mounting angle requirements of approximately 30 and 45 degrees for the emitter beam 367 to the upper housing 2, the mechanical description will begin with the laser head 375 enclosure which includes the hollow sphere 365 of FIG. 17. The electrically conductive hollow sphere 365 is the ideal geometric shape for enclosing the laser head 375 which is normally in the shape of a rectangular block.

The hollow sphere 365 shape is beneficial from a fluid (air or air and rain water in this case) flow standpoint, because wind can be impinging on the sphere from any direction and the flow of the wind over the sphere during freezing rain conditions should have minimal effect on the formation of ice on the conductor C. Also, from a corona discharge standpoint, the sphere shape is ideal because the sphere diameter chosen of 3.5 inches (88.9 mm) does not produce corona at line voltages of 345 kV or even higher. The distance of the hollow sphere 365 from the surface of the conductor C is very important so the fluid flow over the hollow sphere 365 does not affect ice formation on the conductor C. To evaluate the fluid flow effects over the hollow sphere 365 it is necessary to find the values of Reynolds numbers for the hollow sphere 365 for the range of wind velocities normally encountered during freezing rain conditions.

Reynolds number $N_{Re}$ is defined as the product of the outside diameter $D_O$ of the sphere times the velocity of the wind V divided by the kinematic viscosity $\upsilon_f$ of the fluid. Reynolds number is a dimensionless quantity. The normal range of the wind speed is from about one mi/h (0.447 m/sec) up to about 30 mi/h (13.41 m/sec) for most cases where icing has occurred. The values of Reynolds numbers for the sphere 365 without ice can range from 2,890 and up to 86,600 for this range of wind speeds and up to 136,100 for 1.0 inch of radial ice on the sphere. It was found that in the range of $N_{Re}$ from about 1,000 to about 200,000 (69.2 mi/h or 30.9 m/sec) the pattern of flow over the sphere 365 does not change much. The flow separates at a position on the surface of the hollow sphere 365 at about 80 degrees from the front stagnation point where the wind impinges on the hollow sphere 365 and then becomes a fully developed turbulent wake on the back of the hollow sphere 365.

The pressure distribution does not vary much with $N_{Re}$ in this range, so the coefficient of drag remains almost constant at about 0.5. The vortices in the wake break way, drift downstream in the wake flow, degenerate, and new ring vortices form behind the sphere. With this well behaved turbulent wake, it was found that when a distance "Y" of separation between the bottom of the sphere and the surface of the largest conductor C was 6.47 inches (164.34 mm) for the 30 degree mount, where approximately one inch of ice thickness was formed on both the sphere and the conductor C, then there was very little effect on the ice formation process due to the flows over the sphere and the conductor and the turbulent wakes behind each. (See FIG. 24).

Figure 25:
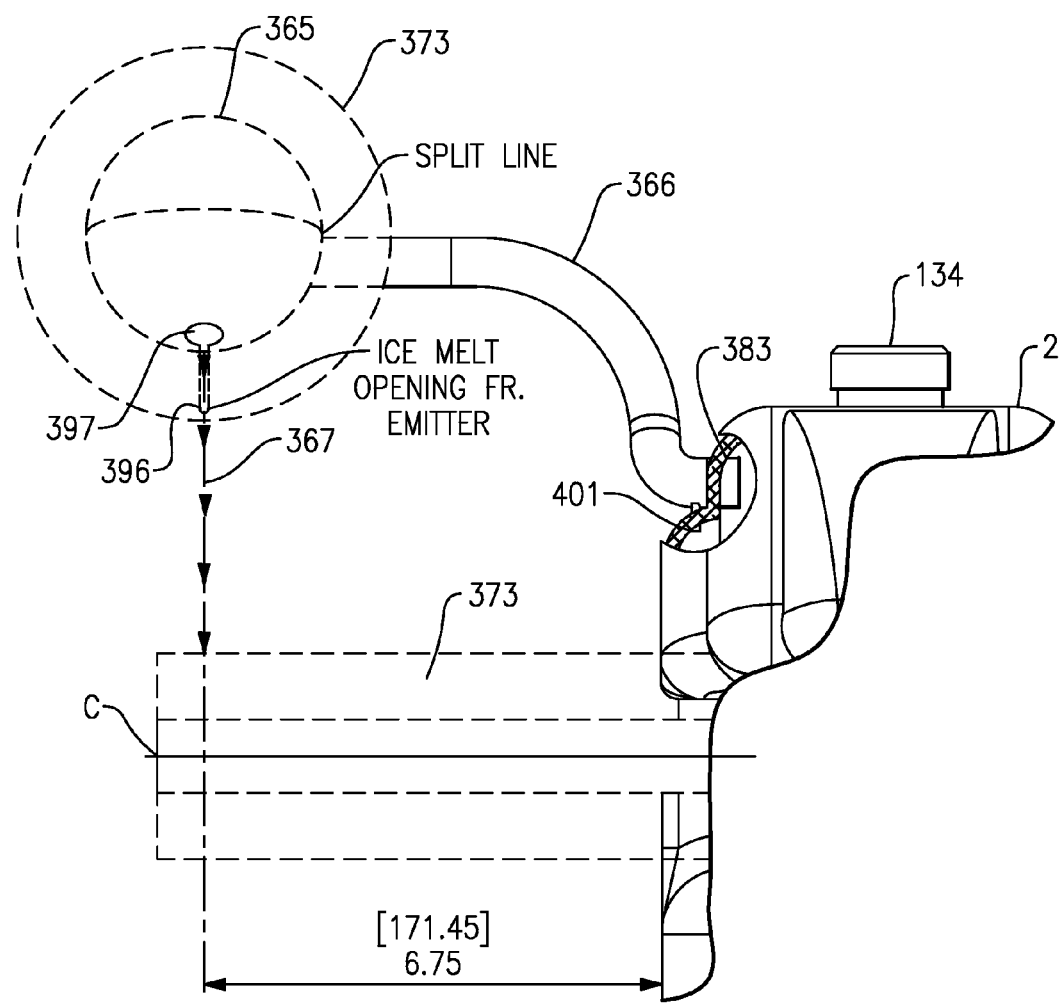
FIG. 25 illustrates a cut away front view of the STR unit with 30° mount.

Also, it was found and shown in FIG. 25, the "X" distance the hollow sphere 365 must be mounted from the outside wall surface of the STR unit 1 to the emitter beam 367, which is the centerline of the hollow sphere 365, in the front view of FIG. 17, was 6.75 inches (171.45 mm) for the wind and rain normal to the conductor at a speed of 30 mi/h or 13.41 msec. For the 45 degree mount the "Y" distances of separation were somewhat greater than for the 30 degree mount. For the 30 degree mount the maximum separation distance is 6.47 inches (164.34 mm) for the largest conductor with 1.00 inch (25.4 mm) of radial ice, and for the smallest conductor with the same thickness of ice this distance is 5.85 inches (148.59 mm). The reason for these smaller maximum distances for the 30 degree mount is because the turbulence wake behind the large diameter sphere is closer to the front of the conductor C before its wake occurs. Although the 30 degree mount results in smaller separation distances at the high normal wind and rain speed of 30 mi/h, care must be exercised to not have the hollow sphere 365 interfere with ice formations during light wind freezing rain conditions, since the hollow sphere 365 may tend to shelter the conductor C below if placed near the top of the conductor C.

For the above reasons it is necessary that the hollow sphere 365 diameter be kept as small as possible so the effects of turbulent flow over the hollow sphere 365 does not impact how ice is formed on the conductor C and does not provide a shelter over the conductor C during light freezing rain. Also, keeping the hollow sphere 365 diameter small reduces the horizontal distance "X" required between the centerline of the sphere and the outside wall of the STR unit 1. The dimensions required for the laser head 375 of FIG. 18 to fit inside the 3.5 inch outside diameter of the sphere are approximately 2.00 inches (50.8 mm) in length, 1.50 inches (38.1 mm) in height, and 1.00 inch (25.4 mm) in depth. There are no commercially available CCD laser heads of these dimensions. The dimensions of currently available heads are considerably larger, typically double the length, and width and approximately 1.5 times larger in depth. Therefore, a completely new design of the laser head 375 was required, or the sphere diameter would have to be twice the size, and mounted at much greater distances from the STR unit 1 and the conductor C, which was impractical. For example, to maintain Reynolds number less than 200,000 with 1.0 inch of radial ice, the outside diameter of the sphere without ice could be 6.00 inches. Therefore, the 'X' and 'Y' dimensions would have to be increased by approximately an additional 3.00 inches.

Under heavy winds of 30 mi/h (13.41 m/sec) the angle of rotation of the STR unit 1 without the ice thickness sensor installed is about 2.2 degrees. However, this rotational motion of the STR unit 1, as will be seen later, is not that important since the emitter beam 367 continues to be directed toward the centerline of the conductor C with the mounting arrangement of standoff bracket 366 and the hollow sphere 365. The reason for this is because the laser head 375 always rotates about the centerline of conductor C. Since the STR unit 1 rotates about the centerline of the conductor C when a wind force is applied and so does the laser head 375, then the emitter beam 367 is always pointed to the centerline of the conductor C for any rotation angle of the STR unit 1.

Figure 24:
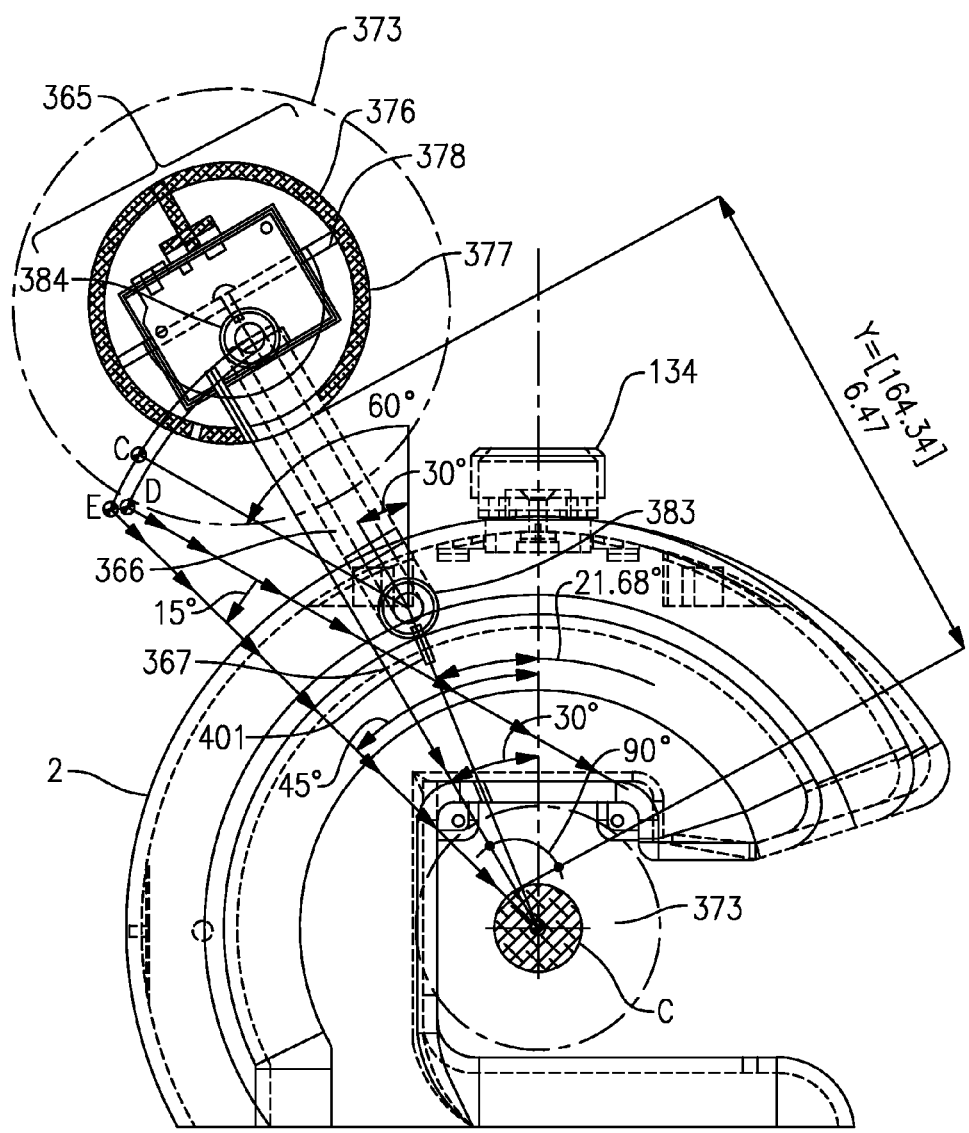
FIG. 24 illustrates a cross-sectional view taken along line R-R of FIG. 17 showing 30° mount and adjustment of emitter beam for 45° mount.

Referring to the FIG. 24, mounting the hollow sphere 365 at an angle of 30 degrees as measured from the vertical centerline of the conductor C and the emitter beam 367 can be adjusted to achieve a 45 degree mounting angle and resolve the issue of certain conductor C strands causing emitter beams 367 to be trapped between their strands of wire. In FIG. 24, the distance from the base of the hollow sphere 365 at the point of exit of the emitter beam 367 from the hollow sphere 365 and normal to the surface of the conductor C is 6.47 inches as measured along the 30 degree angle from the vertical. This distance of the hollow sphere 365 from the surface of the conductor C was needed to not affect the ice buildup process on the conductor C.

The standoff bracket 366 is attached at its lower end to the upper housing 2 at an angle of 21.68 degrees with respect to the vertical centerline of the conductor C. The standoff bracket 366 is tipped backward or to the left 30 degrees from its vertical at attachment point 383. This allows the emitter beam 367 being directed at an angle of 30 degrees from the vertical centerline of the conductor C. The standoff bracket 366 at its top end supports the hollow sphere 365 through a hole contained therein at an attachment point 384.

The hollow sphere 365 can be rotated on the bracket at the attachment point 384. If a 45 degree angle of the emitter beam 367 is desirable, then the standoff bracket 366 is rotated down about its pivot point 383 counterclockwise on the arc of its rotation to a new angle of 60 degrees at point 'C'. Since the hollow sphere 365 has not been rotated about the attachment point 384, then the emitter beam 367 beginning at point 'D' will not be directed through the centerline of the conductor C, but passes by the conductor C on the right side. With the standoff bracket 366 in its new position at point 'C' (or 60 degrees from the vertical) the hollow sphere 365 needs to be rotated clockwise 15 degrees. When the hollow sphere 365 is fixed to the standoff bracket 366 at that attachment point 384 at this new angle of 15 degrees, the emitter beam 367 emerging at point 'E' is now at an angle of 45 degrees with respect to the vertical centerline of the conductor C and is normal to the surface of the conductor C.

This method of mounting the hollow sphere 365 with a rotatable standoff 366 and the rotatable hollow sphere 365 has three advantages. First, only one mounting position of the standoff bracket 366 at its lower end is needed on the upper housing 2 at the pivot point 383. Second, the emitter beam 367 can be adjusted at any angle from 30 degrees to 45 degrees and thus avoid any trapping of its return signal between the strands of any conductor. Third, because the hollow sphere 365 is attached to the standoff bracket 366 whose lower end is mounted at 21.68 degrees with respect to the vertical centerline of the conductor C, it is clearly positioned much higher from the STR unit 1 and away from the turbulence wake of the conductor C than what occurred with the 45 degree mount, even with one inch of ice on both the conductor and the sphere. Therefore, this method achieves about the same separation between the conductor C and the hollow sphere 365 even when the emitter beam 367 is adjusted to 45 degrees to the vertical.

In addition two standoff brackets 366 and two sensor spheres (not necessarily two laser heads 375) can be mounted at the same angle on the left and right sides of the STR unit 1 which minimizes the rotation of the STR unit 1 during high winds about the conductor C due to their counteracting force opposite to this rotation and provides a more even balance when the hollow spheres 365 are covered with ice which results in more accurate ice thickness measurements.

To provide more detail on the standoff bracket 366 mounting to the upper housing 2 and to the hollow sphere 365, a front view of the STR unit 1 with the 30 degree mount and 1.00 inch of radial ice buildup is shown in FIG. 25. The standoff bracket 366 is mounted at a right angle into a hole in the upper housing 2 at the pivot point 383. The standoff bracket 366 on its outside surface is nearly flush with the outside wall of the STR unit 1 at this point. The standoff bracket 366 curves upward and out to the left and enters the lower half of the hollow sphere 365. The horizontal distance "X" of FIGS. 17 and 25 from the outside wall of the STR unit 1 to the emitter beam 367 is 6.75 inches, as mentioned earlier. The standoff bracket 366 is allowed to rotate inside the hole at the pivot point 383 and be fixed to the upper housing 2 using a set screw 401 that is easily accessible between the two upper jaws 6 of FIGS. 2 and 13 when the opening and closing mechanism 39, including the lower jaw 7 is in its fully down position. The set screw 401 is shown in FIGS. 24 and 25.

Figure 26:
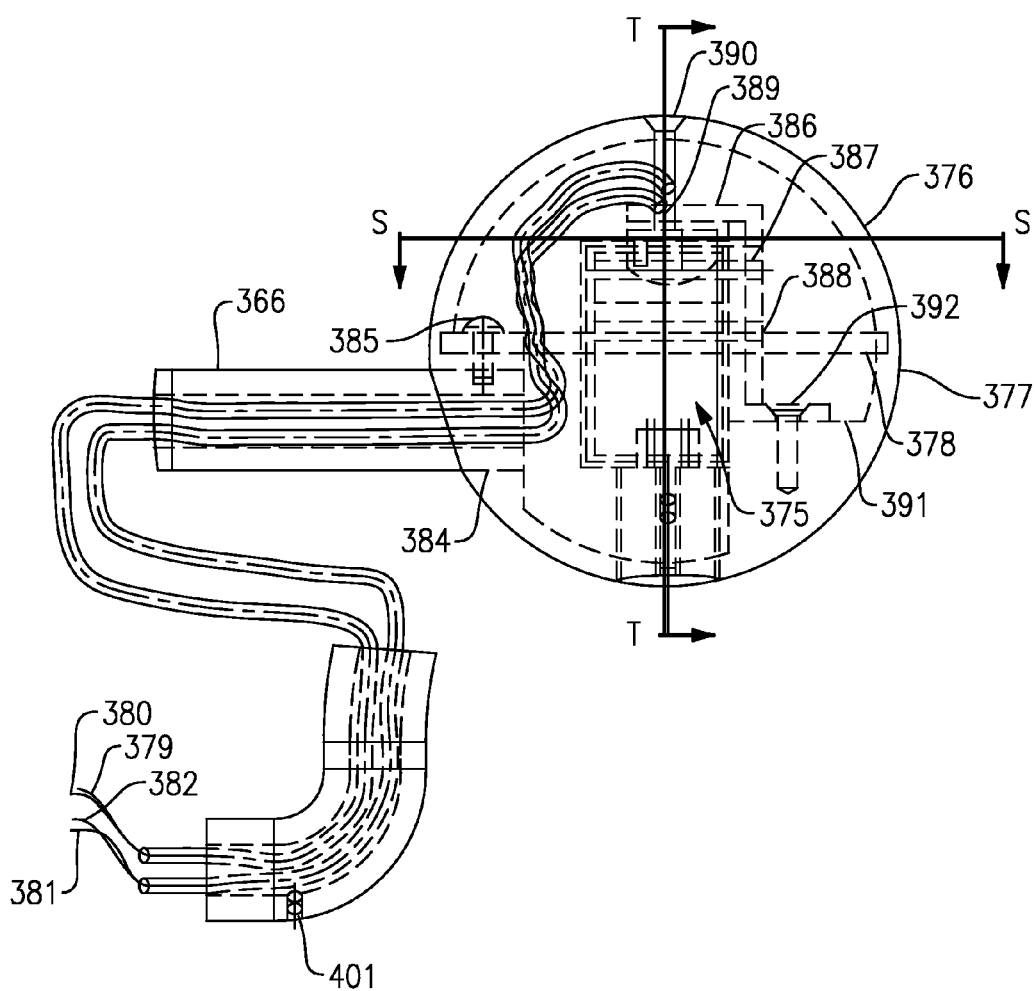
FIG. 26 illustrates a hollow sphere and upper and lower connections of a standoff bracket.

The mechanical construction of the hollow sphere 365 is given in FIG. 26. The hollow sphere 365 includes a top half 376 and a bottom half 377 with their split line at 378 so that access to the laser head 375 of FIG. 26 is available for power supply leads 379 and 380 and for output data leads 381 and 382. FIG. 26 shows the standoff bracket 366 mounted to the bottom half 377 of the hollow sphere 365 which in turn supports the laser head 375. The top end of the standoff bracket 366 fits through the attachment point 384 in the bottom half 377 of the hollow sphere 365 and is kept from turning with the set screw 385.

Referring to FIG. 24, the hollow sphere 365 can be rotated on the standoff bracket 366 to precisely set the angle from 30 degrees to 45 degrees for the emitter beam 367 to be directed toward the centerline of the conductor C and then the set screw 385 of FIG. 25 is tightened down onto the standoff bracket 366.

Figure 27:
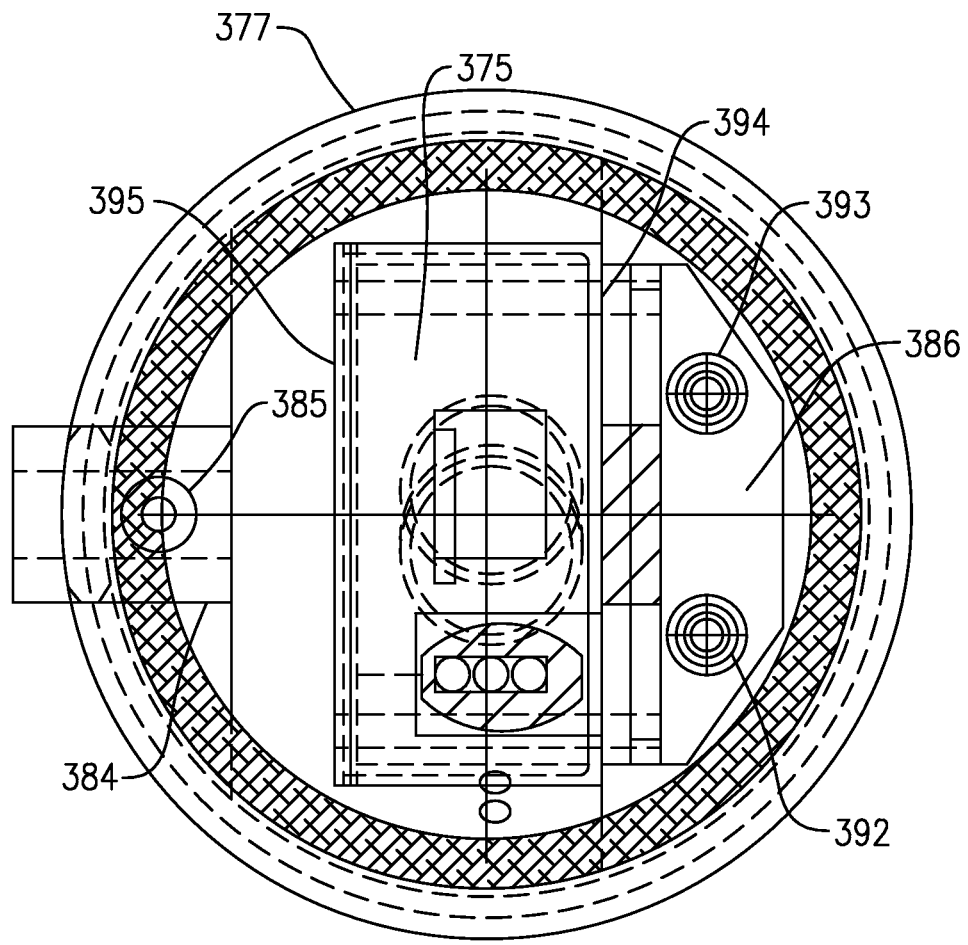
FIG. 27 illustrates a cross-sectional view taken along line S-S of FIG. 26.

The laser head 375 is mounted to a "Z" bracket 386, shown in FIGS. 26 and 27, which serves two purposes. First, the back of the laser head 375 is mounted to the "Z" bracket 386 using holes 387 and 388. Second, a top threaded hole 389 is used to hold down the top half 376 of the hollow sphere 365 with a flat head screw 390. The lower portion of the "Z" bracket 386 is fixed to a step 391 using two flat head screws 392 and 393. The two flat head screws 392 and 393 are shown in FIG. 27.

The laser head 375 is electrostatically shielded by the two halves 376 and 377 of the hollow sphere 365 of FIG. 25 because no electric field is present inside an electrically conducting Faraday cage. The laser head 375 including the electronics therein is electromagnetically shielded with the ferrous box including a box cover 394 and a base of the box 395 shown in FIG. 27.

Figure 28:
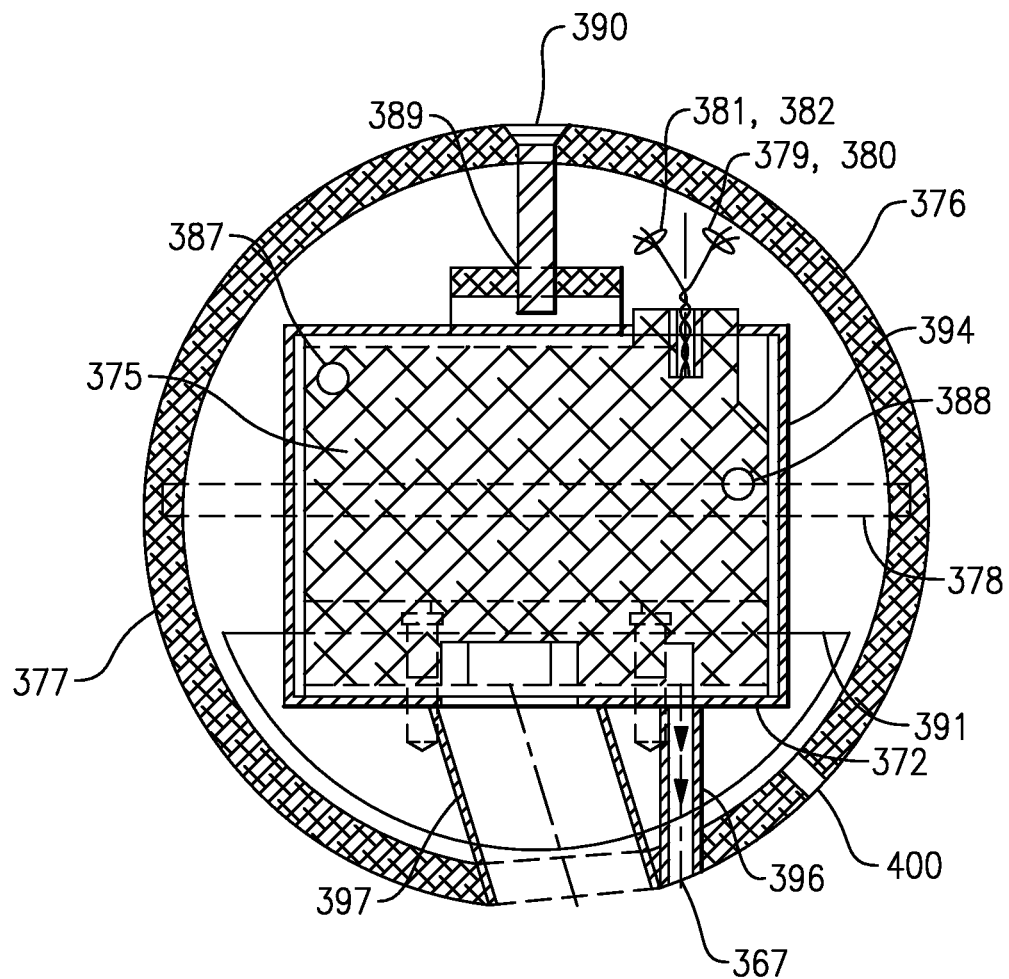
FIG. 28 illustrates a cross-sectional view taken along line T-T of FIG. 26.

The FIG. 28 shows an emitter tube 396 at the base of the laser head 372 which extends down through a hole in the lower half sphere 377. The purpose of the emitter tube 396 which surrounds the emitter beam 367 is to prevent water, dirt and other foreign materials from accumulating inside the lower half sphere 377 and interfering with the emitter beam 367.

Figure 29:
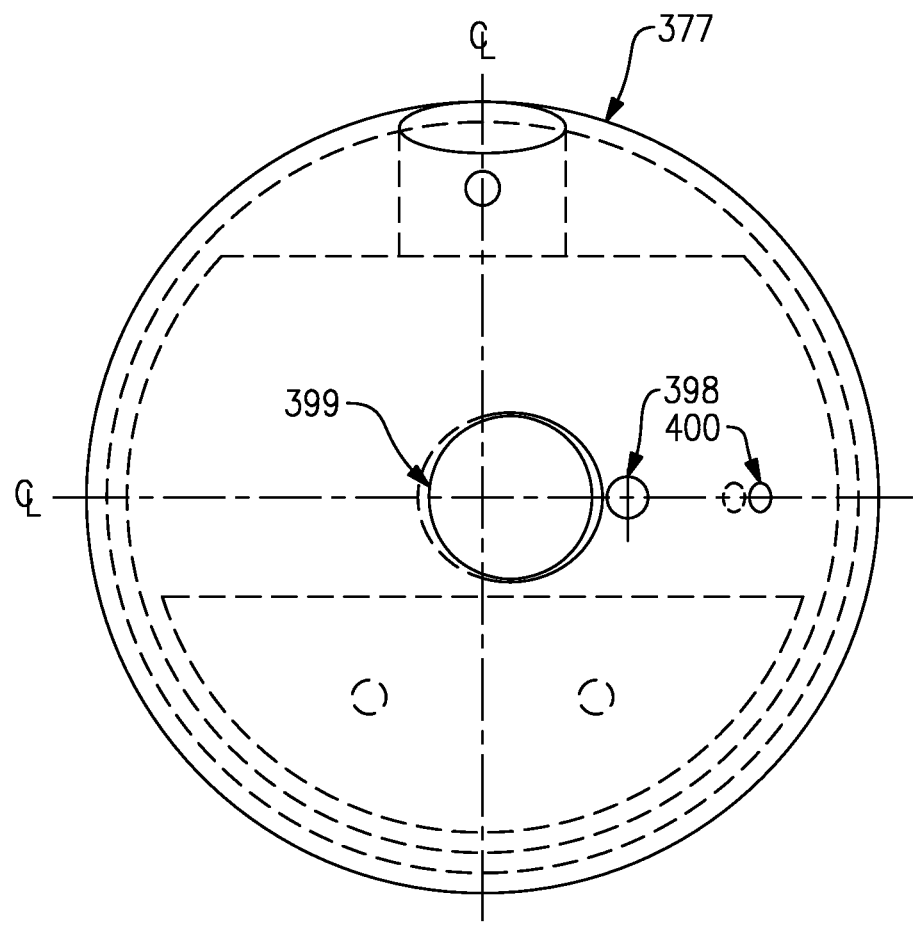
FIG. 29 illustrates a bottom view of FIG. 26.

In addition, a receiver tube 397, like the emitter tube 396, extends down from the base of the laser head 372 and projects through a hole in the lower half sphere 377. The receiver tube 397 also prevents foreign material from entering the cavity inside the bottom of the lower half sphere 377 and interfering with the reflected beam. FIG. 29 shows the emitter hole 398 and the receiver hole 399. In FIG. 28, there is another hole through the bottom half 377 of hollow sphere 365 just to the right of the emitter tube 396, of which when the laser head 375 is rotated clockwise 45 degrees (for the 45 degree mount) points directly down.

A weep hole 400 is a drain for both the upper and lower half spheres 376 and 377 which allows any condensation of water which could accumulate inside to drain out the weep hole 400. As can be seen in FIG. 18, the weep hole 400 is located at the bottom in the lower half of 377 hollow sphere 365 when the emitter is adjusted at 45 degrees to the vertical centerline of the conductor C. The weep hole 400 is provided for in the 30 degree mount.

Referring to FIG. 25 it should be noted that since the receiver tube 397 and the emitter tube 396 both point downward, that even with winds appearing from the left side or the right side of the hollow sphere 365, it would be very difficult for snow, freezing rain and other foreign material to be blown into the receiver tube 397 and the emitter tube 396. Also, the laser beam's heating energy will keep the receiver tube 397 and the emitter tube 396 open and will not become covered with ice even though significant amounts of ice can be covered over the hollow sphere 365 and on the conductor C. This would not be the case for the ultrasonic sensor where ice buildup on the sensor head sphere would prevent the pulse from being emitted and the reflected pulse from the target conductor C being received unless the sensor enclosure is heated.

Figure 30:
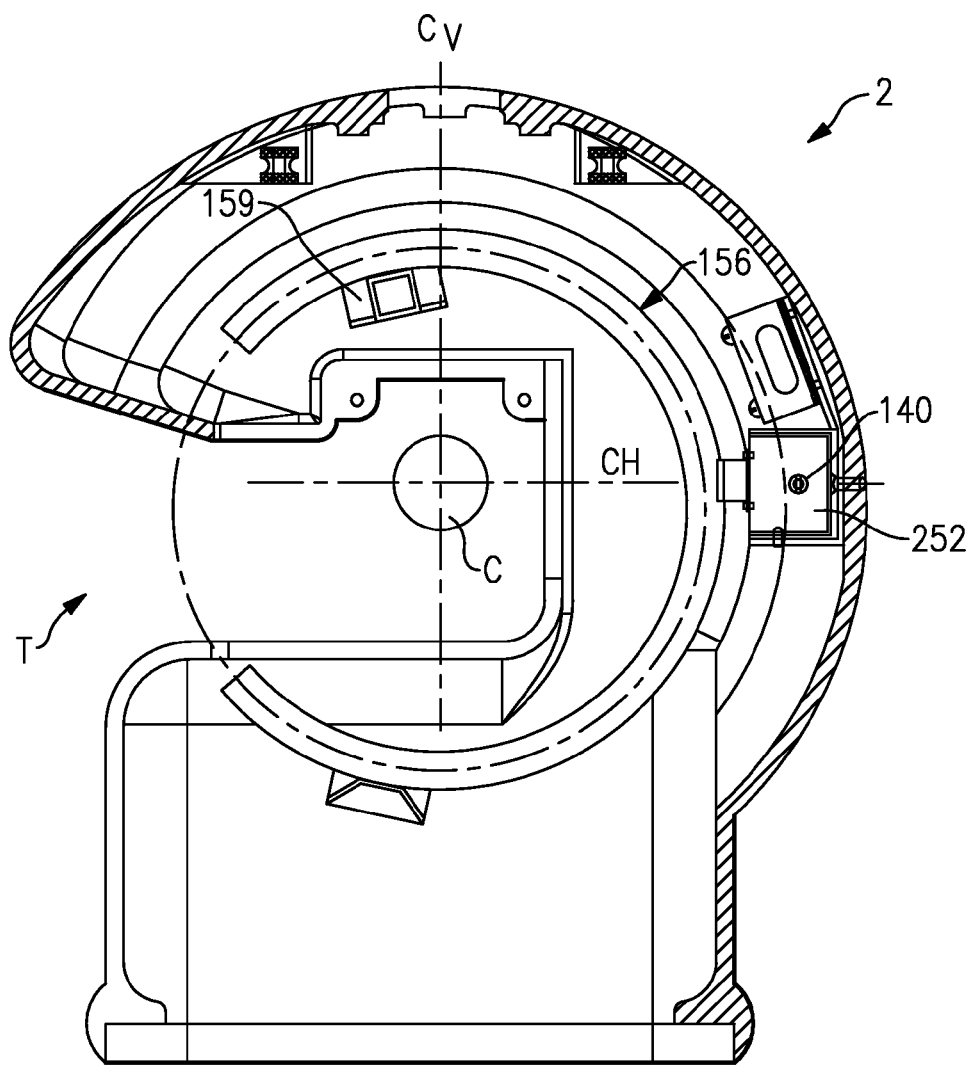
FIG. 30 illustrates a cross-sectional view of an example upper housing including an example "C" loop coil for measuring the power line frequency current taken along line E-E of FIG. 2.
Figure 31:
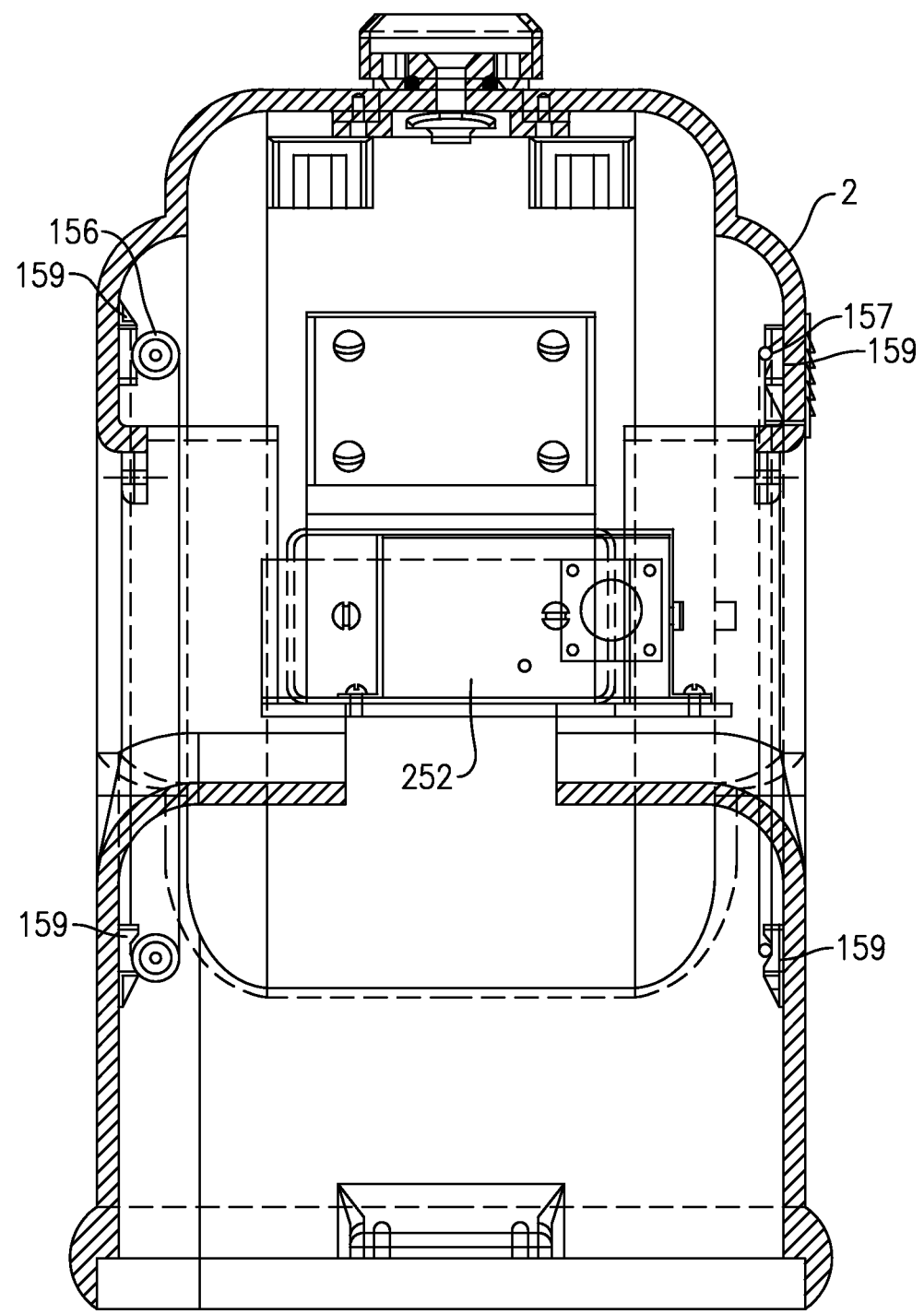
FIG. 31 illustrates a cross-sectional view of the example upper housing showing the "C" loop coil of FIG. 30 and an example electric power line sag sensor for measuring sag of the line taken along line F-F of FIG. 1.

The sag of the conductor C can be determined by measuring the slope (inclination) angle of the conductor C between the horizontal at the point of attachment of the conductor C at the tower structure or pole, and the conductor C; and the line span length (the distance between these supporting structures). If ice accumulates on the conductor C, then the combined weight of the ice and the conductor C will cause the slope angle to increase. Since the slope angle is being measured by the sag sensor 252, shown in FIGS. 30 and 31, then the weight of the ice per unit length can be calculated between these supporting structures and an average radial thickness of ice over the conductor C can be found.

This calculated thickness is compared to the thickness of ice as measured from the laser head 375. If the laser output data indicates a thinner thickness of ice than the average radial thickness as determined by the increased sag calculation, then the ice formation shape is eccentric as shown in FIG. 16 (*b*), (*c*) or (*d*). If the ice thickness as measured by the laser output data is in close agreement with calculated average radial ice thickness, then the ice formation is approximately radial as shown in FIG. 16 (*a*).

The STR unit 1 is also able to predict when ice will begin to form on the conductor C, since the STR unit 1 measures the rate of rainfall with an infrared optical rain sensor assembly 138 shown in FIG. 1, an ambient temperature sensor assembly 307 of FIG. 12, and an adjustable conductor temperature probe assembly 273 shown in FIG. 13. If the magnitude of current, which is also being measured by the "C" loop coil 156 of FIG. 13 flowing in the conductor C results in enough heating due to the $I^2R$ losses during freezing rain conditions such that the measured surface conductor C temperature is maintained above the freezing temperature of ice on the conductor C, then ice will not form on the conductor C. However, the current magnitude may not be high enough to prevent ice from forming on the conductor C, in which case based on the measured rate of rainfall, ambient and conductor C temperatures, the software algorithms of the remote offsite locations predicts the rate of growth of the ice thickness. Since the ice thickness is being measured, the predicted and actual thicknesses are compared and the magnitude and time to melt the ice is calculated on a real time basis.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A device for attaching to an electric power line conductor comprising:
   an electrically conductive housing including an opening for accepting the power line conductor and configured to be grounded to the power line conductor;
   at least one magnetic core configured to surround the power line conductor and power a power supply module; and
   a laser triangulation distance measuring device configured to be powered by the power supply module, wherein the distance measuring device is located inside a capsule including a laser beam emitter and an opening for a laser emitter beam and an opening for a laser receiver beam located near the bottom of the capsule, and the capsule is mounted to a standoff bracket attached to the housing.

2. The device of claim 1 wherein the distance measuring device is electrostatically shielded for preventing corona discharges when the housing is mounted on the electric power line conductor.

3. The device of claim 2 wherein the distance measuring device is electrostatically shielded by an electrically conducting sphere surrounding the distance measuring device and the sphere is attached to the housing.

4. The device of claim 1 wherein the distance measuring device is configured to be electromagnetically shielded from a load current and a fault current of the electric power line conductor.

5. The device of claim 4 wherein the distance measuring device is electromagnetically shielded from the load current and the fault current by a ferrous material that surrounds the distance measuring device.

6. A device for attaching to an electric power line conductor comprising:
   an electrically conductive housing including an opening for accepting the power line conductor and configured to be grounded to the power line conductor;
   at least one magnetic core configured to surround the power line conductor and power a power supply module; and
   a laser triangulation distance measuring device configured to be powered by the power supply module, wherein the distance measuring device is located inside a sphere, the sphere including a laser beam emitter and an opening for a laser emitter beam and an opening for a laser receiver beam located near the bottom of the sphere, and the sphere is mounted to a standoff bracket attached to the housing.

7. The device of claim 6 wherein the sphere is spaced from the housing with the standoff bracket for preventing interference with ice formation on the electric power line conductor.

8. The device of claim 6 wherein an outside diameter of the sphere containing the laser distance measuring device is shaped to have a Reynolds number below 200,000 during freezing rain conditions.

9. The device of claim 7 wherein an outside diameter of the sphere is 3.5 inches (88.9 mm) and is mounted laterally from a vertical centerline a distance of not less than 6.75 inches (171.45 mm) from an outside surface of the housing and mounted vertically a distance of not less than 8.00 inches (203.2 mm) as measured from the centerline of the electric power line conductor to a horizontal centerline of the sphere.

10. The device of claim 6 wherein the standoff bracket is mounted at a lower end to the housing and is rotatable with respect to the housing.

11. The device of claim 6 wherein the sphere is mounted to a top end of the standoff bracket and is rotatable with respect to the standoff bracket.

12. The device of claim 6 wherein the sphere is rotatably connected at a top end of the standoff bracket and a bottom end of the standoff bracket is rotatable with respect to the housing.

13. The device of claim 6 wherein the standoff bracket is rotatable with respect to the housing at a point of connection to the housing, and the sphere is rotatable with respect to the standoff bracket at a point of connection for allowing the emitter beam to be adjusted normal to a surface of the electric power line conductor and directed toward a centerline of the electric power line conductor.

14. The device of claim 6 wherein the laser beam emitter is configured to point normal to at least one strand of wire on the surface of the electric power line conductor.

15. The device of claim 13 wherein the rotatable standoff bracket and the rotatable sphere are configured to be adjusted such that a flow of air and rain water over the sphere and a turbulence wake of the sphere does not materially alter a flow of air and rain water over the electric power line conductor and a turbulence wake of the electric power line conductor, and the laser beam emitter is configured to be directed normal to the electric power line conductor.

16. The device of claim 13 wherein the rotatable standoff bracket and the rotatable sphere are configured to be adjusted such that a flow of air and turbulence wakes over the sphere and the electric power line conductor do not materially alter the natural formation of ice on the electric power line conductor, and the laser beam emitter is configured to point normal to the electric power line conductor.

17. The device of claim 6 wherein the standoff bracket is rotatable and tubular and is configured to allow power supply leads from the housing to reach the laser distance measuring device and data output leads from the laser distance measuring to the housing.

18. The device of claim 6 wherein the sphere includes a top sphere half and a bottom sphere half split along a horizontal centerline of the sphere configured to allow access to the bottom sphere half for attachment to an upper end of the standoff bracket for positioning the laser beam emitter normal to the electric power line conductor.

19. The device of claim 6 wherein the opening for the laser emitter beam includes an emitter tube and the opening for the laser receiver beam includes a receiver tube, the emitter tube and the receiver tube penetrate through the bottom of the sphere, and prevent water, foreign matter, and freezing rain from entering the sphere.

20. The device of claim 6 wherein the distance measuring device is a first distance measuring device and including a second distance measuring device located in a second sphere attached to the housing with a second standoff bracket configured to counteract a rotational force of the sphere from wind.

21. A method of measuring ice thickness on an electric power line conductor comprising:
   measuring ice thickness on an electric power line conductor with a laser distance measuring device to determine laser ice thickness measurements, wherein the laser distance measuring device is located in a capsule mounted to a standoff bracket attached to a housing and emits a laser beam normal to the electric power line conductor;

processing ice thickness measurements with a sensor electronics module; and transmitting data representative of the ice thickness measurements to a remote location with an onboard transmitter-receiver unit and an antenna for analysis.

22. The method of claim 21 including measuring ice thickness on the electric power line conductor by measuring a sag in the electric power line conductor based on the measured slope of the electric power line conductor to determine sag ice thickness measurements.

23. The method of claim 22 including determining an ice formation profile by comparing the laser ice thickness measurements with the sag ice thickness measurements.

24. The method of claim 21 including determining a magnitude of line current and time needed to de-ice the electric power line conductor.

25. The method of claim 21 including determining a rate of ice buildup on the electric power line conductor.

\* \* \* \* \*